United States Patent
Zhirnov et al.

(10) Patent No.: US 7,381,185 B2
(45) Date of Patent: Jun. 3, 2008

(54) METHOD AND APPARATUS FOR DETECTING PHYSIOLOGIC SIGNALS

(75) Inventors: Yevgeniy N. Zhirnov, Poulsbo, WA (US); Vadim I. Pougatchev, Poulsbo, WA (US); Evgueni N. Gribkov, Kingston, WA (US)

(73) Assignee: MedDorna, LLC, Austin, TX (US)

( * ) Notice: Subject to any disclaimer, the term of this patent is extended or adjusted under 35 U.S.C. 154(b) by 360 days.

(21) Appl. No.: 10/861,566

(22) Filed: Jun. 4, 2004

(65) Prior Publication Data
US 2005/0251055 A1 Nov. 10, 2005

Related U.S. Application Data

(63) Continuation of application No. 10/842,294, filed on May 10, 2004, now abandoned.

(51) Int. Cl.
A61B 5/04 (2006.01)
(52) U.S. Cl. .......... 600/300; 600/509; 600/544; 600/546; 128/920
(58) Field of Classification Search ......... 600/509, 600/300, 301, 521, 544, 546; 128/920
See application file for complete search history.

(56) References Cited

U.S. PATENT DOCUMENTS

| | | | |
|---|---|---|---|
| 4,805,629 A | 2/1989 | Farges | |
| 5,299,119 A | 3/1994 | Kraf et al. | |
| 5,419,338 A | 5/1995 | Sarma et al. | |
| 5,492,117 A | 2/1996 | Eisenberg et al. | |
| 5,643,212 A | 7/1997 | Coutre et al. | |
| 5,738,104 A * | 4/1998 | Lo et al. ............ | 600/521 |
| 5,902,250 A | 5/1999 | Verrier et al. | |
| 5,984,954 A | 11/1999 | Cohen | |
| 6,055,541 A | 4/2000 | Solecki et al. | |
| 6,113,549 A | 9/2000 | Johnson | |
| 6,161,037 A | 12/2000 | Cohen | |

(Continued)

OTHER PUBLICATIONS

Task Force of the European Society of Cardiology and the North American Society of Pacing and Electrophysiology, "Special Report: Heart Rate Variability, Standards of Measurement, Physiological Interpretation, and Clinical Use," Circulation, vol. 93, No. 5 (Mar. 1, 1996), pp. 1043-1065.

(Continued)

Primary Examiner—Kennedy J. Schaetzle
(74) Attorney, Agent, or Firm—Michael P. Adams; Winstead PC

(57) ABSTRACT

The invention analyzes relationships between factors, within a patient population, to identify autonomic dysfunction patterns. Patient test results are then compared with the identified patterns to determine the patient's autonomic function. The invention can continually amend the patient population with new test results to create increasingly accurate normative data sets from which a patient's autonomic function can be more accurately assessed. The invention may apply this concept in an application service provider model. An embodiment of the invention may use a novel method of identifying certain components on physiological signals such as the R-wave for an ECG. The method locates R-waves by searching for maximum slope values and cycle lengths that satisfy certain threshold values. Another embodiment of the invention entails a non-provocative HRV test whereby certain time domain and frequency domain factors are analyzed to determine a patient's autonomic function.

60 Claims, 31 Drawing Sheets

U.S. PATENT DOCUMENTS

| | | |
|---|---|---|
| 6,302,844 B1 | 10/2001 | Walker et al. |
| 6,346,886 B1 | 2/2002 | De La Huerga |
| 6,358,201 B1 | 3/2002 | Childre et al. |
| 6,416,473 B1 | 7/2002 | Risk et al. |
| 6,438,409 B1 | 8/2002 | Malik et al. |
| 6,490,480 B1 | 12/2002 | Lerner |
| 6,507,644 B1 | 1/2003 | Henderson et al. |
| 6,602,191 B2 | 8/2003 | Quy |
| 6,650,932 B1 | 11/2003 | Menzie et al. |
| 6,875,418 B2 | 4/2005 | Hampton |
| 2002/0098540 A1 | 7/2002 | Pennica et al. |
| 2004/0078220 A1 | 4/2004 | Jackson |
| 2005/0148895 A1 | 7/2005 | Misczynski et al. |
| 2006/0030907 A1 | 2/2006 | McNew |

OTHER PUBLICATIONS

Pan et al., "A Real-Time QRS Detection Algorithm," IEEE Transactions of Biomedical Engineering, vol. BME-32, No. 3 (Mar. 1985), pp. 230-236.

GE Healthcare, "Cardiology: Innovative Pay-Per-Use Program Guards Against Obsolescence and Monitor Replacement Costs," printed from Internet site: http://www.gehealthcare.com/cgi-bin/print/print.cgi, pp. 1-3.

L.A. Lipsitz et al., "Heart rate and Respiratory Rhythm Dynamics on Ascent to High Altitude," British Heart Journal, vol. 74, Copyright 1995, pp. 1-2.

Anna M. Bianchi et al., "Non-Conventional Measurements from ECG Recordings: Towards an Improvement of Diagnostic Properties," International Journal of Bioelectromagnetism, vol. 5, No. 1, 2003, pp. 171-174.

GE Medical Systems Information Technologies, DINAMAP PRO 1000 Series Blood Pressure, Oximetry & Temperature, pp. 1-2.

B. Mazzanti et al., "Validation of an ECG-Derived Respiration Monitoring Method," DEIS University of Bologna, Mortara Rangoni Europe, Blogna, Italy, pp. 1-5.

George B. Moody et al., "Clinical Validation of the ECG-Derived Respiration (EDR) Technicque," Washington, D.C. IEEE Computer Society Press, 1986, pp. 1-13.

A.P. Rocha et al., "A Study on the Estimation of the Respiratory Signal in 12-Lead Holter Recordings," pp. 1-2.

S. Leanderson et al., "Estimation of the Respiratory Frequency Using Spatial Information in the VCG," Medical Engineering Physics, Copyright 2003, pp. 501-507.

Sonia Gouveia et al., "Matlab Implementation of a Method for the Estimation of the Respiratory Signal in 24h-Holter Recordings," p. 1.

T. Penzel et al., "Systematic Comparison of Different Algorithms for Apnoea Detection Based on Electrocardiogram Recordings," Medical & Biological Engineering & Computing 2002, vol. 40, pp. 402-407.

GE Healthcare, "Radiology PACS: ASP as a New Delivery Model or Healthcare Applications," printed from Internet site: http://www.gehealthcare.com/cgi-bin/print/print.cgi, pp. 1-3.

PCT International Search Report, PCT/US2005/16023, mailed Jul. 26, 2006.

PCT Written Opinion of the International Searching Authority, PCT/US2005/16023, mailed Jul. 26, 2006.

PCT International Search Report, PCT/US2005/015513, mailed Jun. 7, 2006.

PCT Written Opinion of the International Searching Authority, PCT/US2005/015513, mailed Jun. 7, 2006.

* cited by examiner

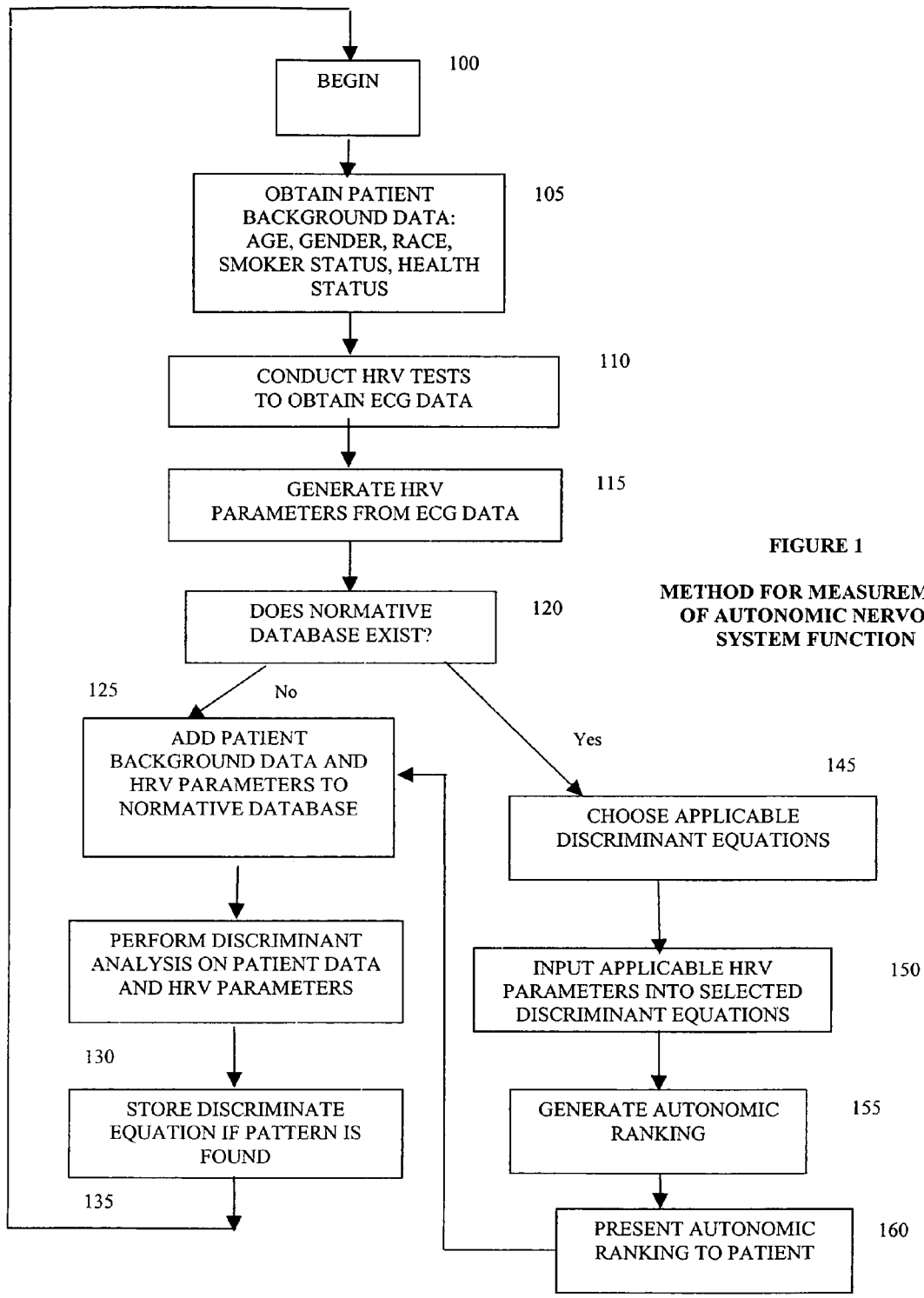

Subject Questionnaire

Subject must complete the following information list:                                       Subject ID: _____

Personal Questions:

1. Age: ____    2. Sex: ☐ Male  ☐ Female    3. Height (ft-in): ____ - ____    4. Weight (lb): ____

5. How long in the USA (yrs): ____

6. Check your parent's most accurate belonging to Hispanic / Latino ethnicity:

| Father | Mother | | Father | Mother | | Father | Mother | |
|---|---|---|---|---|---|---|---|---|
| ☐ | ☐ | Central American | ☐ | ☐ | Mexican | ☐ | ☐ | South American |
| ☐ | ☐ | Cuban | ☐ | ☐ | Puerto Rican | ☐ | ☐ | Other Hispanic |
| | | | | | | ☐ | ☐ | Non-Hispanic |

7. Check your parent's most accurate belonging to specific races:

| Father | Mother | American Indian / Alaska Native | Father | Mother | Asian | Father | Mother | Black / African American | Father | Mother | Native Hawaiian / Pacific Islander | Father | Mother | White | | |
|---|---|---|---|---|---|---|---|---|---|---|---|---|---|---|---|---|
| ☐ | ☐ | Alaskan | ☐ | ☐ | Cambodian | ☐ | ☐ | African American | ☐ | ☐ | Hawaiian | ☐ | ☐ | Afghani | | Persian |
| ☐ | ☐ | Central American | ☐ | ☐ | Chinese | ☐ | ☐ | Caribbean | ☐ | ☐ | Guamian | | | Anglo-Saxon | | Scandinavian |
| ☐ | ☐ | North American | ☐ | ☐ | Indian | ☐ | ☐ | Central African | ☐ | ☐ | Samoan | | | Arabian | | Semitic |
| ☐ | ☐ | South American | ☐ | ☐ | Indonesian | ☐ | ☐ | East African | ☐ | ☐ | Other NH/PI | | | Armenian | | Eastern Slavic |
| | | | ☐ | ☐ | Japanese | ☐ | ☐ | North African | | | | | | Balkan | | Western Slavic |
| | | Type in your tribe name: | ☐ | ☐ | Korean | ☐ | ☐ | South African | | | | | | Baltic | | Spanish |
| | | | ☐ | ☐ | Malaysian | ☐ | ☐ | West African | | | | | | French | | Turkish |
| | | | ☐ | ☐ | Pakistani | | | | | | | | | German | | Other White |
| | | | ☐ | ☐ | Philippino | | | | | | | | | Greek | | |
| | | | ☐ | ☐ | Thai | | | | | | | | | Irish | | |
| | | | ☐ | ☐ | Vietnamese | | | | | | | | | Italian | | |
| | | | ☐ | ☐ | Other Asian | | | | | | | | | | | |

Figure 2: Patient Background Information

Patient Questionnaire

Health Questions:

8. Did you have a physical exam (including blood test) within past 6 months?   ☐ No   ☐ Yes 9. Select any of the following that you now or have experienced in the past:

A. Symptoms / Complaints:

| | | | | | | |
|---|---|---|---|---|---|---|
| ☐ Anxiety / Panic Attack | ☐ Backache | ☐ Chest Pain | ☐ Cold Feet / Hands | ☐ Colic |
| ☐ Depression | ☐ Digestive Problems | ☐ Dizziness | ☐ Extreme Fatigue | ☐ Growing Pains |
| ☐ Headache | ☐ Insomnia | ☐ Leg Pain | ☐ Loss of Memory | ☐ Nausea / Vomit |
| ☐ Neck Aches | ☐ Nervousness | ☐ Numbness / Tingling | ☐ Shortness of Breath | ☐ Sinus Trouble |
| ☐ Tension | ☐ Vision Problems | | | |

B. Medical Conditions / Diagnosis

| | | | |
|---|---|---|---|
| ☐ Allergies | ☐ Arthritis | ☐ Asthma | ☐ Cancer | ☐ Diabetes |
| ☐ Epilepsy | ☐ Heart Disease | ☐ Hepatitis | ☐ High Blood Pressure | ☐ Multiple Sclerosis |
| ☐ Muscular Dystrophy | ☐ Parkinson Disease | ☐ Rheumatism | | |

10. Alcohol consumption per week:    Bottles of beer: ___   Glasses of wine: ___   Mixed/Other drinks: ___

11. Smoking:  ☐ No  ☐ Yes    If yes, how many cigarettes per day: ___

If female, enter (where applicable):

12. Day of period: ___    13. Week of pregancy: ___    14. Month of nursing: ___

Figure 3: Patient Health Information

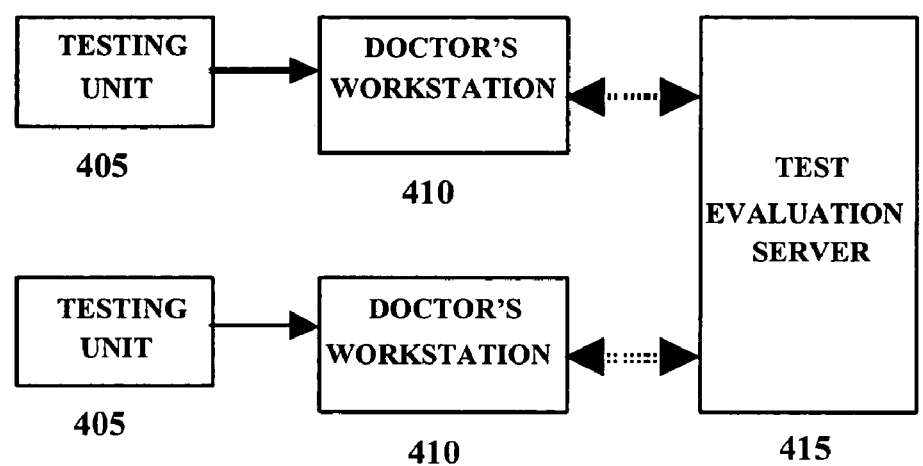
Figure 4: Example of internet-based HRV testing system.

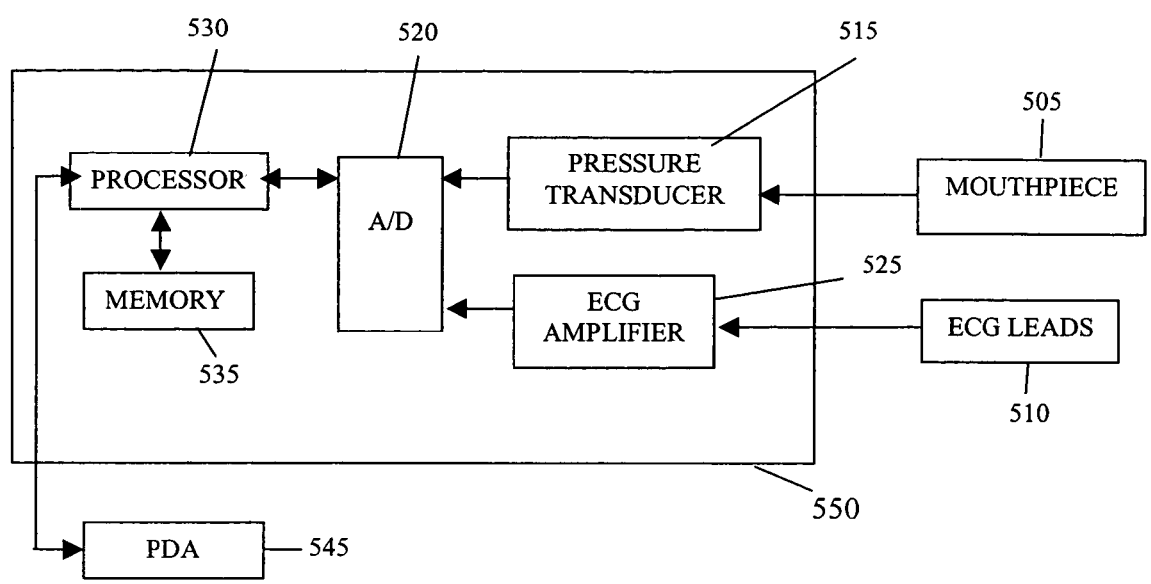
Figure 5: Example Bock Diagram of Testing Unit

FIG. 6A

|    | STATUS   | RMS-SD | TP      | LFnorm | HFnorm | LF/HF    | E/I Ratio | SD    |
|----|----------|--------|---------|--------|--------|----------|-----------|-------|
| 1  | DIABETES | 50.93  | 380.94  | 30     | 70     | 0.428571 | 1.1889    | 62.12 |
| 2  | DIABETES | 58.039 | 389     | 29.75  | 70.25  | 0.423488 | 1.239     | 56.41 |
| 3  | DIABETES | 10.065 | 181.622 | 31.695 | 68.305 | 0.464022 | 1.116     | 35.25 |
| 4  | DIABETES | 52.93  | 382.94  | 25.31  | 74.69  | 0.338867 | 1.19      | 62.15 |
| 5  | DIABETES | 60.039 | 400     | 36     | 64     | 0.5625   | 1.24      | 58    |
| 6  | DIABETES | 10.07  | 182     | 32     | 68     | 0.470588 | 1.116     | 35.3  |
| 7  | DIABETES | 51.93  | 598     | 30     | 70     | 0.428571 | 1.18      | 62    |
| 8  | DIABETES | 51.9   | 687     | 30.15  | 69.85  | 0.431639 | 1.1889    | 62.12 |
| 9  | DIABETES | 58     | 220     | 25     | 75     | 0.333333 | 1.239     | 56.41 |
| 10 | DIABETES | 10.065 | 182.678 | 29.75  | 70.25  | 0.423488 | 1.116     | 35.25 |
| 11 | DIABETES | 52.93  | 648     | 31.695 | 68.305 | 0.464022 | 1.19      | 62.15 |
| 12 | DIABETES | 60.039 | 247     | 38     | 62     | 0.612903 | 1.24      | 58    |
| 13 | DIABETES | 10.07  | 182     | 22.36  | 77.64  | 0.287996 | 1.116     | 35.3  |
| 14 | DIABETES | 51.93  | 378     | 32     | 68     | 0.470588 | 1.18      | 62    |
| 15 | DIABETES | 59     | 268     | 40     | 60     | 0.666667 | 1.22      | 61    |
| 16 | DIABETES | 10     | 181     | 46     | 54     | 0.851852 | 1.114     | 35    |
| 17 | DIABETES | 11     | 182     | 29.75  | 70.25  | 0.423488 | 1.125     | 36    |
| 18 | DIABETES | 51.91  | 770     | 31.695 | 68.305 | 0.464022 | 1.1889    | 62.12 |
| 19 | DIABETES | 59     | 381     | 42.65  | 57.35  | 0.743679 | 1.239     | 56.41 |
| 20 | DIABETES | 10.065 | 184.678 | 31     | 69     | 0.449275 | 1.116     | 35.25 |
| 21 | DIABETES | 52.93  | 299     | 42     | 58     | 0.724138 | 1.19      | 62.15 |
| 22 | DIABETES | 60.039 | 384     | 32     | 68     | 0.470588 | 1.24      | 58    |
| 23 | DIABETES | 10.07  | 182     | 44     | 56     | 0.785714 | 1.116     | 35.3  |
| 24 | DIABETES | 51.93  | 378     | 44.4   | 55.6   | 0.798561 | 1.18      | 62    |
| 25 | DIABETES | 51.94  | 780     | 29.75  | 70.25  | 0.423488 | 1.1889    | 62.12 |
| 26 | DIABETES | 59.1   | 380     | 31.695 | 68.305 | 0.464022 | 1.239     | 56.41 |
| 27 | DIABETES | 10.065 | 182.6   | 36.65  | 63.35  | 0.578532 | 1.116     | 35.25 |
| 28 | DIABETES | 52.93  | 278     | 31     | 69     | 0.449275 | 1.19      | 62.15 |
| 29 | DIABETES | 60.039 | 155     | 32     | 68     | 0.470588 | 1.24      | 58    |
| 30 | DIABETES | 10.07  | 182     | 31     | 69     | 0.449275 | 1.116     | 35.3  |
| 31 | DIABETES | 51.93  | 794     | 22.36  | 77.64  | 0.287996 | 1.18      | 62    |
| 32 | DIABETES | 59     | 382     | 30     | 70     | 0.428571 | 1.223     | 47    |
| 33 | DIABETES | 25.25  | 379     | 65.3   | 34.7   | 1.881844 | 1.123     | 45.23 |
| 34 | DIABETES | 43.15  | 389     | 62.4   | 37.6   | 1.659574 | 1.234     | 51.23 |
| 35 | DIABETES | 35.12  | 181     | 61.32  | 38.68  | 1.585315 | 1.156     | 65.52 |
| 36 | DIABETES | 45.18  | 380     | 70.2   | 29.8   | 2.355705 | 1.22      | 64.25 |
| 37 | DIABETES | 54.78  | 405     | 65     | 35     | 1.857143 | 1.17      | 55.55 |
| 38 | DIABETES | 32.12  | 190     | 72     | 28     | 2.571429 | 1.18      | 54.12 |
| 39 | DIABETES | 22.16  | 600     | 70.94  | 29.06  | 2.441156 | 1.15      | 32.32 |
| 40 | DIABETES | 24.26  | 700     | 69.58  | 30.42  | 2.287311 | 1.19      | 39.34 |
| 41 | DIABETES | 28.46  | 230     | 60.35  | 39.65  | 1.522068 | 1.14      | 41.02 |
| 42 | DIABETES | 27.98  | 184     | 70.25  | 29.75  | 2.361345 | 1.187     | 63.25 |
| 43 | DIABETES | 45.56  | 650     | 71.94  | 28.06  | 2.563792 | 1.244     | 71.25 |
| 44 | DIABETES | 35.46  | 250     | 60     | 40     | 1.5      | 1.211     | 70.02 |

FIG. 6B

|  | STATUS | RMS-SD | TP | LFnorm | HFnorm | LF/HF | E/I Ratio | SD |
|---|---|---|---|---|---|---|---|---|
| 45 | DIABETES | 37.48 | 190 | 80 | 20 | 4 | 1.201 | 34.56 |
| 46 | DIABETES | 35.24 | 389 | 70.25 | 29.75 | 2.361345 | 1.222 | 45.12 |
| 47 | DIABETES | 33.25 | 267 | 63.25 | 36.75 | 1.721088 | 1.189 | 47.18 |
| 48 | DIABETES | 21.24 | 182 | 64.25 | 35.75 | 1.797203 | 1.245 | 43.26 |
| 49 | DIABETES | 20.21 | 182 | 64.36 | 35.64 | 1.805836 | 1.248 | 43.46 |
| 50 | DIABETES | 36.38 | 779 | 71 | 29 | 2.448276 | 1.188 | 55.23 |
| 51 | DIABETES | 47.56 | 390 | 63 | 37 | 1.702703 | 1.177 | 41.95 |
| 52 | DIABETES | 35.47 | 187 | 78 | 22 | 3.545455 | 1.165 | 33.28 |
| 53 | DIABETES | 24.22 | 320 | 73 | 27 | 2.703704 | 1.128 | 39.15 |
| 54 | DIABETES | 54.24 | 398 | 66 | 34 | 1.941176 | 1.1364 | 41.23 |
| 55 | DIABETES | 51.2 | 399 | 76 | 24 | 3.166667 | 1.211 | 45.11 |
| 56 | DIABETES | 47.45 | 350 | 70.25 | 29.75 | 2.361345 | 1.239 | 36.31 |
| 57 | DIABETES | 24.35 | 790 | 70.26 | 29.74 | 2.362475 | 1.237 | 32.15 |
| 58 | DIABETES | 24.26 | 394 | 61.25 | 38.75 | 1.580645 | 1.235 | 31.24 |
| 59 | DIABETES | 27.28 | 200 | 78.23 | 21.77 | 3.593477 | 1.236 | 30.12 |
| 60 | DIABETES | 27.39 | 230 | 70.36 | 29.64 | 2.373819 | 1.237 | 34.69 |
| 61 | DIABETES | 31.29 | 190 | 68 | 32 | 2.125 | 1.122 | 38.15 |
| 62 | DIABETES | 31.89 | 185 | 69.68 | 30.32 | 2.298153 | 1.126 | 39.12 |
| 63 | DIABETES | 32.56 | 845 | 61.23 | 38.77 | 1.579314 | 1.238 | 41.32 |
| 64 | DIABETES | 33.46 | 425 | 62.54 | 37.46 | 1.669514 | 1.24 | 41.36 |
| 65 | HEALTHY | 119.14 | 2300 | 29 | 71 | 0.408451 | 1.68 | 153.9755 |
| 66 | HEALTHY | 120 | 2000 | 30 | 70 | 0.428571 | 1.681 | 153.8888 |
| 67 | HEALTHY | 63.34 | 1500.03 | 32 | 68 | 0.470588 | 1.603 | 138.509 |
| 68 | HEALTHY | 86.78 | 3331.34 | 26 | 74 | 0.351351 | 1.62 | 141.3 |
| 69 | HEALTHY | 121 | 2589 | 36 | 64 | 0.5625 | 1.688 | 154 |
| 70 | HEALTHY | 65 | 3244 | 32 | 68 | 0.470588 | 1.62 | 139 |
| 71 | HEALTHY | 125 | 2999 | 30 | 70 | 0.428571 | 1.611 | 158 |
| 72 | HEALTHY | 70.8 | 3400 | 30.15 | 69.85 | 0.431639 | 1.59 | 152 |
| 73 | HEALTHY | 70.7 | 2498.7 | 25 | 75 | 0.333333 | 1.57 | 151 |
| 74 | HEALTHY | 119.18 | 1902.56 | 29.75 | 70.25 | 0.423488 | 1.685 | 153.8812 |
| 75 | HEALTHY | 63.34 | 2500 | 31.695 | 68.305 | 0.464022 | 1.603 | 138.509 |
| 76 | HEALTHY | 86.78 | 3331.34 | 38 | 62 | 0.612903 | 1.65 | 141.3 |
| 77 | HEALTHY | 126 | 2456 | 22.36 | 77.64 | 0.287996 | 1.688 | 154 |
| 78 | HEALTHY | 65 | 2220 | 40.52 | 59.48 | 0.681237 | 1.62 | 135 |
| 79 | HEALTHY | 121 | 3125 | 40 | 60 | 0.666667 | 1.611 | 170 |
| 80 | HEALTHY | 70.8 | 2400 | 46 | 54 | 0.851852 | 1.59 | 152 |
| 81 | HEALTHY | 119.111 | 1902.56 | 29.75 | 70.25 | 0.423488 | 1.689 | 153.9456 |
| 82 | HEALTHY | 63.34 | 2899 | 50.29 | 49.71 | 1.011668 | 1.603 | 138.509 |
| 83 | HEALTHY | 86.78 | 3331.34 | 42.65 | 57.35 | 0.743679 | 1.7 | 141.3 |
| 84 | HEALTHY | 128 | 2698 | 31 | 69 | 0.449275 | 1.688 | 154 |
| 85 | HEALTHY | 65 | 2487 | 42 | 58 | 0.724138 | 1.62 | 140 |
| 86 | HEALTHY | 129 | 2789 | 32 | 68 | 0.470588 | 1.611 | 171 |
| 87 | HEALTHY | 70.8 | 2777 | 44 | 56 | 0.785714 | 1.59 | 152 |
| 88 | HEALTHY | 70.7 | 2498.7 | 44.4 | 55.6 | 0.798561 | 1.57 | 152 |
| 89 | HEALTHY | 119.119 | 2902.35 | 29.75 | 70.25 | 0.423488 | 1.675 | 153.9999 |

FIG. 6C

|  | STATUS | RMS-SD | TP | LFnorm | HFnorm | LF/HF | E/I Ratio | SD |
|---|---|---|---|---|---|---|---|---|
| 90 | HEALTHY | 63.34 | 3458.59 | 55.56 | 44.44 | 1.250225 | 1.603 | 138.509 |
| 91 | HEALTHY | 86.78 | 3331.34 | 36.65 | 63.35 | 0.578532 | 1.61 | 141.3 |
| 92 | HEALTHY | 119 | 2945.36 | 31 | 69 | 0.449275 | 1.688 | 154 |
| 93 | HEALTHY | 65 | 3215.25 | 32 | 68 | 0.470588 | 1.62 | 141 |
| 94 | HEALTHY | 122.356 | 3000.02 | 31 | 69 | 0.449275 | 1.611 | 159 |
| 95 | HEALTHY | 70.8 | 2400 | 22.36 | 77.64 | 0.287996 | 1.59 | 152 |
| 96 | HEALTHY | 121 | 4056 | 30 | 70 | 0.428571 | 1.611 | 160 |
| 97 | HEALTHY | 121 | 2932.569 | 32 | 68 | 0.470588 | 1.611 | 158 |
| 98 | HEALTHY | 119.14 | 2300 | 29 | 71 | 0.408451 | 1.68 | 153.9755 |
| 99 | HEALTHY | 120 | 2000 | 28 | 72 | 0.388889 | 1.681 | 153.8888 |
| 100 | HEALTHY | 63.34 | 1500.03 | 50.1 | 49.9 | 1.004008 | 1.603 | 138.509 |
| 101 | HEALTHY | 86.78 | 3331.34 | 24.26 | 75.74 | 0.320306 | 1.62 | 141.3 |
| 102 | HEALTHY | 121 | 2589 | 38 | 62 | 0.612903 | 1.688 | 154 |
| 103 | HEALTHY | 65 | 3244 | 30 | 70 | 0.428571 | 1.62 | 139 |
| 104 | HEALTHY | 125 | 2999 | 32 | 68 | 0.470588 | 1.611 | 158 |
| 105 | HEALTHY | 70.8 | 3400 | 60.23 | 39.77 | 1.514458 | 1.59 | 152 |
| 106 | HEALTHY | 70.7 | 2498.7 | 25 | 75 | 0.333333 | 1.57 | 151 |
| 107 | HEALTHY | 119.18 | 1902.56 | 30.25 | 69.75 | 0.433692 | 1.685 | 153.8812 |
| 108 | HEALTHY | 63.34 | 2500 | 32.25 | 67.75 | 0.476015 | 1.603 | 138.509 |
| 109 | HEALTHY | 86.78 | 3331.34 | 60.74 | 39.26 | 1.547122 | 1.65 | 141.3 |
| 110 | HEALTHY | 126 | 2456 | 23.25 | 76.75 | 0.302932 | 1.688 | 154 |
| 111 | HEALTHY | 65 | 2220 | 32.45 | 67.55 | 0.480385 | 1.62 | 135 |
| 112 | HEALTHY | 121 | 3125 | 41.26 | 58.74 | 0.702417 | 1.611 | 170 |
| 113 | HEALTHY | 70.8 | 2400 | 47.48 | 52.52 | 0.904037 | 1.59 | 152 |
| 114 | HEALTHY | 119.111 | 1902.56 | 28.75 | 71.25 | 0.403509 | 1.689 | 153.9456 |
| 115 | HEALTHY | 63.34 | 2899 | 30.945 | 69.055 | 0.448121 | 1.603 | 138.509 |
| 116 | HEALTHY | 86.78 | 3331.34 | 40.25 | 59.75 | 0.67364 | 1.7 | 141.3 |
| 117 | HEALTHY | 128 | 2698 | 54.52 | 45.48 | 1.198769 | 1.688 | 154 |
| 118 | HEALTHY | 65 | 2487 | 45.59 | 54.41 | 0.837897 | 1.62 | 140 |
| 119 | HEALTHY | 129 | 2789 | 29.98 | 70.02 | 0.428163 | 1.611 | 171 |
| 120 | HEALTHY | 70.8 | 2777 | 48.56 | 51.44 | 0.944012 | 1.59 | 152 |
| 121 | HEALTHY | 70.7 | 2498.7 | 48.21 | 51.79 | 0.930875 | 1.57 | 152 |
| 122 | HEALTHY | 119.119 | 2902.35 | 52.23 | 47.77 | 1.093364 | 1.675 | 153.9999 |
| 123 | HEALTHY | 63.34 | 3458.59 | 25.65 | 74.35 | 0.34499 | 1.603 | 138.509 |
| 124 | HEALTHY | 86.78 | 3331.34 | 39.25 | 60.75 | 0.646091 | 1.61 | 141.3 |
| 125 | HEALTHY | 119 | 2945.36 | 29.15 | 70.85 | 0.411433 | 1.688 | 154 |
| 126 | HEALTHY | 65 | 3215.25 | 24.56 | 75.44 | 0.325557 | 1.62 | 141 |
| 127 | HEALTHY | 122.356 | 3000.02 | 38.26 | 61.74 | 0.619695 | 1.611 | 159 |
| 128 | HEALTHY | 70.8 | 2400 | 25.68 | 74.32 | 0.345533 | 1.59 | 152 |

FIG. 6D

| | STATUS | 30:15 Ratio | NN | SDNN | VLF | LF | HF | NNmin SB |
|---|---|---|---|---|---|---|---|---|
| 1 | DIABETES | 1.235 | 862 | 53.6 | 213.6642 | 652.32 | 1522.08 | 616 |
| 2 | DIABETES | 1.287 | 860 | 50.8 | 300 | 506.345 | 1195.655 | 796 |
| 3 | DIABETES | 1.182 | 790 | 51.9 | 127.0011 | 435.8158 | 939.2142 | 532 |
| 4 | DIABETES | 1.296 | 860 | 49.8 | 213.6704 | 538.4298 | 1588.91 | 600 |
| 5 | DIABETES | 1.289 | 865 | 48.9 | 169 | 717.3504 | 1275.29 | 580 |
| 6 | DIABETES | 1.18 | 869 | 50.1 | 110 | 997.7642 | 2120.249 | 550 |
| 7 | DIABETES | 1.278 | 864 | 55.5 | 239.4186 | 562.737 | 1313.053 | 700 |
| 8 | DIABETES | 1.269 | 850 | 49 | 233.9176 | 625.5371 | 1449.213 | 730 |
| 9 | DIABETES | 1.287 | 851 | 45.2 | 142 | 377.3525 | 1132.058 | 680 |
| 10 | DIABETES | 1.182 | 854 | 44 | 97.30658 | 199.9379 | 472.1222 | 578 |
| 11 | DIABETES | 1.247 | 859 | 43.96 | 244.9982 | 649.0502 | 1398.75 | 592 |
| 12 | DIABETES | 1.289 | 869 | 36.58 | 125 | 762.7436 | 1244.476 | 658 |
| 13 | DIABETES | 1.181 | 866 | 30.58 | 99.78 | 468.8892 | 1628.111 | 612 |
| 14 | DIABETES | 1.236 | 778 | 36.5 | 180.0256 | 521.6 | 1108.4 | 623 |
| 15 | DIABETES | 1.28 | 779 | 37.8 | 120 | 690 | 1035 | 684 |
| 16 | DIABETES | 1.18 | 880 | 32.35 | 55.0896 | 506 | 594 | 724 |
| 17 | DIABETES | 1.188 | 875 | 31.36 | 142.3022 | 209.0116 | 493.5484 | 689 |
| 18 | DIABETES | 1.245 | 873 | 39.56 | 234.6695 | 745.9862 | 1607.654 | 678 |
| 19 | DIABETES | 1.287 | 865 | 40.1 | 132.24 | 893.9355 | 1202.045 | 625 |
| 20 | DIABETES | 1.182 | 836 | 42.5 | 112.23 | 491.8956 | 1094.864 | 624 |
| 21 | DIABETES | 1.278 | 853 | 44.44 | 182.9992 | 793.3296 | 1095.55 | 599 |
| 22 | DIABETES | 1.289 | 859 | 51.48 | 212 | 853.1264 | 1812.894 | 726 |
| 23 | DIABETES | 1.188 | 878 | 49.26 | 98 | 638.88 | 813.12 | 720 |
| 24 | DIABETES | 1.284 | 873 | 47.43 | 223.808 | 556.6428 | 697.0572 | 580 |
| 25 | DIABETES | 1.296 | 879 | 33.89 | 230.1308 | 496.3044 | 1171.946 | 594 |
| 26 | DIABETES | 1.287 | 861 | 35.28 | 300 | 1088.815 | 2346.475 | 577 |
| 27 | DIABETES | 1.182 | 877 | 30.333 | 65.25 | 1012.72 | 1750.5 | 588 |
| 28 | DIABETES | 1.281 | 899 | 35 | 169.1333 | 804.2516 | 1790.108 | 645 |
| 29 | DIABETES | 1.289 | 898 | 35.369 | 37.43475 | 809.8496 | 1720.93 | 625 |
| 30 | DIABETES | 1.1897 | 888 | 45.87 | 110.11 | 698.9818 | 1555.798 | 619 |
| 31 | DIABETES | 1.269 | 875 | 46.21 | 247.8114 | 252.8916 | 878.1084 | 684 |
| 32 | DIABETES | 1.28 | 859 | 35.39 | 215 | 810 | 1890 | 675 |
| 33 | DIABETES | 1.189 | 862 | 50 | 210.23 | 110.2068 | 58.56319 | 600 |
| 34 | DIABETES | 1.126 | 854 | 36 | 256.35 | 82.7736 | 49.8764 | 610 |
| 35 | DIABETES | 1.299 | 859 | 45.59 | 125.03 | 34.3208 | 21.6492 | 620 |
| 36 | DIABETES | 1.264 | 864 | 48.23 | 198.23 | 127.6025 | 54.16746 | 630 |
| 37 | DIABETES | 1.185 | 870 | 51.23 | 168.36 | 153.816 | 82.824 | 740 |
| 38 | DIABETES | 1.234 | 878 | 32.56 | 120 | 50.4 | 19.6 | 720 |
| 39 | DIABETES | 1.2 | 887 | 39.15 | 240 | 255.384 | 104.616 | 654 |
| 40 | DIABETES | 1.211 | 854 | 42.15 | 235.68 | 323.0739 | 141.2461 | 586 |
| 41 | DIABETES | 1.236 | 851 | 37.29 | 145.68 | 50.88712 | 33.43288 | 687 |
| 42 | DIABETES | 1.245 | 845 | 42.15 | 98.69 | 59.93028 | 25.37973 | 623 |
| 43 | DIABETES | 1.281 | 879 | 44.26 | 256.36 | 283.1846 | 110.4554 | 642 |
| 44 | DIABETES | 1.263 | 881 | 49.25 | 169.36 | 48.384 | 32.256 | 649 |

FIG. 6E

| | STATUS | 30:15 Ratio | NN | SDNN | VLF | LF | HF | NNmin SB |
|---|---|---|---|---|---|---|---|---|
| 45 | DIABETES | 1.245 | 865 | 43.21 | 100.35 | 71.72 | 17.93 | 687 |
| 46 | DIABETES | 1.278 | 859 | 36.12 | 190.25 | 139.6219 | 59.12813 | 702 |
| 47 | DIABETES | 1.256 | 867 | 37.89 | 135.25 | 83.33188 | 48.41813 | 711 |
| 48 | DIABETES | 1.212 | 866 | 37.45 | 57.36 | 80.0812 | 44.5588 | 623 |
| 49 | DIABETES | 1.246 | 839 | 45.12 | 150.26 | 20.42786 | 11.31214 | 645 |
| 50 | DIABETES | 1.239 | 841 | 42.31 | 250.34 | 375.3486 | 153.3114 | 690 |
| 51 | DIABETES | 1.248 | 829 | 50 | 140.25 | 157.3425 | 92.4075 | 689 |
| 52 | DIABETES | 1.284 | 874 | 43.12 | 114.26 | 56.7372 | 16.0028 | 674 |
| 53 | DIABETES | 1.264 | 840 | 44.44 | 189.35 | 95.3745 | 35.2755 | 598 |
| 54 | DIABETES | 1.234 | 836 | 46.21 | 210.23 | 123.9282 | 63.8418 | 578 |
| 55 | DIABETES | 1.245 | 839 | 36.36 | 100.25 | 227.05 | 71.7 | 534 |
| 56 | DIABETES | 1.284 | 845 | 46.23 | 220.31 | 91.10723 | 38.58278 | 596 |
| 57 | DIABETES | 1.267 | 824 | 48.2 | 210.36 | 407.2551 | 172.3849 | 578 |
| 58 | DIABETES | 1.234 | 810 | 47.25 | 298.23 | 58.65913 | 37.11088 | 569 |
| 59 | DIABETES | 1.247 | 842 | 40.12 | 70.25 | 101.5034 | 28.24658 | 610 |
| 60 | DIABETES | 1.236 | 812 | 39.98 | 160.24 | 49.08314 | 20.67686 | 623 |
| 61 | DIABETES | 1.248 | 862 | 39.21 | 39.25 | 102.51 | 48.24 | 627 |
| 62 | DIABETES | 1.239 | 818 | 34.58 | 112.12 | 50.78278 | 22.09722 | 638 |
| 63 | DIABETES | 1.247 | 880 | 36.31 | 250.35 | 364.1042 | 230.5458 | 659 |
| 64 | DIABETES | 1.294 | 835 | 38.89 | 222.35 | 126.7373 | 75.91269 | 645 |
| 65 | HEALTHY | 1.568 | 886 | 40.56 | 125.6 | 630.576 | 1543.824 | 650 |
| 66 | HEALTHY | 1.5988 | 885 | 55.69 | 298 | 510.6 | 1191.4 | 620 |
| 67 | HEALTHY | 1.5 | 880 | 60.45 | 125 | 440.0096 | 935.0204 | 556 |
| 68 | HEALTHY | 1.45 | 870 | 59.58 | 1204 | 553.1084 | 1574.232 | 600 |
| 69 | HEALTHY | 1.599 | 890 | 58.98 | 596.36 | 717.3504 | 1275.29 | 500 |
| 70 | HEALTHY | 1.555 | 887 | 60.25 | 125.987 | 997.7642 | 2120.249 | 777 |
| 71 | HEALTHY | 1.618 | 899 | 40.12 | 1123.21 | 562.737 | 1313.053 | 775 |
| 72 | HEALTHY | 1.46 | 900 | 43.25 | 1325.25 | 625.5371 | 1449.213 | 745 |
| 73 | HEALTHY | 1.468 | 901 | 57.96 | 989.29 | 377.3525 | 1132.058 | 510 |
| 74 | HEALTHY | 1.5562 | 859 | 66.39 | 1230.5 | 199.9379 | 472.1222 | 630 |
| 75 | HEALTHY | 1.5 | 845 | 68.15 | 452.2 | 649.0502 | 1398.75 | 614 |
| 76 | HEALTHY | 1.45 | 865 | 69.12 | 1324.12 | 762.7436 | 1244.476 | 514 |
| 77 | HEALTHY | 1.599 | 867 | 63.25 | 359 | 468.8892 | 1628.111 | 800 |
| 78 | HEALTHY | 1.551 | 896 | 58.9 | 590 | 660.476 | 969.524 | 700 |
| 79 | HEALTHY | 1.618 | 869 | 70.1 | 1400 | 690 | 1035 | 625 |
| 80 | HEALTHY | 1.52 | 870 | 63.45 | 1300 | 506 | 594 | 645 |
| 81 | HEALTHY | 1.512 | 893 | 68.48 | 1200 | 209.0116 | 493.5484 | 678 |
| 82 | HEALTHY | 1.5 | 894 | 69.37 | 545.36 | 1183.646 | 1169.994 | 698 |
| 83 | HEALTHY | 1.55 | 899 | 45.96 | 1235.36 | 893.9355 | 1202.045 | 659 |
| 84 | HEALTHY | 1.599 | 910 | 87.61 | 1111.24 | 491.8956 | 1094.864 | 600 |
| 85 | HEALTHY | 1.552 | 783 | 56.3 | 598.12 | 793.3296 | 1095.55 | 645 |
| 86 | HEALTHY | 1.618 | 873 | 55.55 | 122.98 | 853.1264 | 1812.894 | 687 |
| 87 | HEALTHY | 1.46 | 854 | 59.63 | 1325 | 638.88 | 813.12 | 698 |
| 88 | HEALTHY | 1.54 | 864 | 39.39 | 1245 | 556.6428 | 697.0572 | 589 |
| 89 | HEALTHY | 1.522 | 869 | 38 | 1234.1 | 496.3044 | 1171.946 | 584 |

FIG. 6F

| | STATUS | 30:15 Ratio | NN | SDNN | VLF | LF | HF | NNmin SB |
|---|---|---|---|---|---|---|---|---|
| 90 | HEALTHY | 1.5 | 894 | 33 | 23.3 | 1908.647 | 1526.643 | 678 |
| 91 | HEALTHY | 1.56 | 900 | 45.96 | 568.12 | 1012.72 | 1750.5 | 594 |
| 92 | HEALTHY | 1.599 | 874 | 40 | 351 | 804.2516 | 1790.108 | 678 |
| 93 | HEALTHY | 1.554 | 865 | 39 | 684.47 | 809.8496 | 1720.93 | 645 |
| 94 | HEALTHY | 1.618 | 896 | 40 | 745.24 | 698.9818 | 1555.798 | 635 |
| 95 | HEALTHY | 1.49 | 900 | 38 | 1269 | 252.8916 | 878.1084 | 600 |
| 96 | HEALTHY | 1.618 | 856 | 59.12 | 1356 | 810 | 1890 | 620 |
| 97 | HEALTHY | 1.618 | 789 | 56.32 | 1200 | 554.4221 | 1178.147 | 580 |
| 98 | HEALTHY | 1.568 | 886 | 40.56 | 1254 | 306.385 | 750.115 | 650 |
| 99 | HEALTHY | 1.5988 | 885 | 55.69 | 359 | 463.68 | 1192.32 | 620 |
| 100 | HEALTHY | 1.5 | 880 | 60.45 | 987 | 282.063 | 280.937 | 556 |
| 101 | HEALTHY | 1.45 | 870 | 59.58 | 1201 | 517.7084 | 1616.292 | 600 |
| 102 | HEALTHY | 1.599 | 890 | 58.98 | 445 | 836 | 1364 | 500 |
| 103 | HEALTHY | 1.555 | 887 | 60.25 | 168 | 972.6 | 2269.4 | 777 |
| 104 | HEALTHY | 1.618 | 899 | 40.12 | 1126 | 606.4 | 1288.6 | 775 |
| 105 | HEALTHY | 1.46 | 900 | 43.25 | 1329 | 1282.297 | 846.7033 | 745 |
| 106 | HEALTHY | 1.468 | 901 | 57.96 | 1011 | 362 | 1086 | 510 |
| 107 | HEALTHY | 1.5562 | 859 | 66.39 | 1239 | 239.58 | 552.42 | 630 |
| 108 | HEALTHY | 1.5 | 845 | 68.15 | 468 | 543.735 | 1142.265 | 614 |
| 109 | HEALTHY | 1.45 | 865 | 69.12 | 1354 | 1220.874 | 789.126 | 514 |
| 110 | HEALTHY | 1.599 | 867 | 63.25 | 458 | 488.9475 | 1614.053 | 800 |
| 111 | HEALTHY | 1.551 | 896 | 58.9 | 684 | 7390.163 | 15383.84 | 700 |
| 112 | HEALTHY | 1.618 | 869 | 70.1 | 1542 | 708.0216 | 1007.978 | 625 |
| 113 | HEALTHY | 1.52 | 870 | 63.45 | 1450 | 521.3304 | 576.6696 | 645 |
| 114 | HEALTHY | 1.512 | 893 | 68.48 | 1320 | 180.55 | 447.45 | 678 |
| 115 | HEALTHY | 1.5 | 894 | 69.37 | 654 | 678.005 | 1512.995 | 698 |
| 116 | HEALTHY | 1.55 | 899 | 45.96 | 1253 | 842.835 | 1251.165 | 659 |
| 117 | HEALTHY | 1.599 | 910 | 87.61 | 1245 | 764.9156 | 638.0844 | 600 |
| 118 | HEALTHY | 1.552 | 783 | 56.3 | 645 | 912.7118 | 1089.288 | 645 |
| 119 | HEALTHY | 1.618 | 873 | 55.55 | 199 | 794.47 | 1855.53 | 687 |
| 120 | HEALTHY | 1.46 | 854 | 59.63 | 145 | 1132.905 | 1200.095 | 698 |
| 121 | HEALTHY | 1.54 | 864 | 39.39 | 1245 | 628.1763 | 674.8237 | 589 |
| 122 | HEALTHY | 1.522 | 869 | 38 | 1475 | 807.4758 | 738.5242 | 584 |
| 123 | HEALTHY | 1.5 | 894 | 33 | 50.25 | 819.4534 | 2375.297 | 678 |
| 124 | HEALTHY | 1.56 | 900 | 45.96 | 640 | 1156.698 | 1790.303 | 594 |
| 125 | HEALTHY | 1.599 | 874 | 40 | 451 | 8676.206 | 21087.79 | 678 |
| 126 | HEALTHY | 1.554 | 865 | 39 | 780 | 7769.556 | 23865.44 | 645 |
| 127 | HEALTHY | 1.618 | 896 | 40 | 740 | 11675.8 | 18841.2 | 635 |
| 128 | HEALTHY | 1.49 | 900 | 38 | 1201 | 358.4928 | 1037.507 | 600 |

FIG. 6G

| | STATUS | NNmax SB | VARmax | VARmean | NNmin Standing | NNmax Standing | Tmax | Trec |
|---|---|---|---|---|---|---|---|---|
| 1 | DIABETES | 772 | 116 | 75.33334 | 592 | 731.12 | 14 | 50 |
| 2 | DIABETES | 1056 | 216 | 157.3333 | 692 | 890.604 | 15 | 49 |
| 3 | DIABETES | 716 | 150 | 74.22222 | 516 | 609.912 | 8.112 | 28.7 |
| 4 | DIABETES | 888 | 250 | 300 | 502 | 650.592 | 14 | 48 |
| 5 | DIABETES | 750 | 169 | 290 | 545 | 702.505 | 12 | 29.1 |
| 6 | DIABETES | 780 | 178 | 270 | 584 | 689.12 | 14 | 20.4 |
| 7 | DIABETES | 930 | 245 | 310 | 597 | 762.966 | 12 | 25.5 |
| 8 | DIABETES | 940 | 187 | 190 | 587 | 744.903 | 11 | 41.1 |
| 9 | DIABETES | 900 | 450 | 222 | 578 | 743.886 | 13.5 | 20.3 |
| 10 | DIABETES | 1000 | 444 | 241 | 514 | 607.548 | 13.5 | 26 |
| 11 | DIABETES | 800 | 215 | 198 | 640 | 798.08 | 12.4 | 32 |
| 12 | DIABETES | 859 | 142 | 235 | 658 | 848.162 | 10.2 | 25 |
| 13 | DIABETES | 830 | 158 | 265 | 632 | 746.392 | 12 | 47 |
| 14 | DIABETES | 999 | 358 | 289 | 647 | 799.692 | 6.5 | 25 |
| 15 | DIABETES | 800 | 136 | 245 | 694 | 888.32 | 7.8 | 14 |
| 16 | DIABETES | 1002 | 296 | 268 | 555 | 654.9 | 9.8 | 16 |
| 17 | DIABETES | 987 | 198 | 247 | 532 | 632.016 | 9.9 | 21 |
| 18 | DIABETES | 952 | 169 | 286 | 547 | 681.015 | 10.2 | 31 |
| 19 | DIABETES | 858 | 178 | 294 | 568 | 731.016 | 12.12 | 24 |
| 20 | DIABETES | 900 | 289 | 289 | 512 | 605.184 | 3.6 | 12 |
| 21 | DIABETES | 956 | 125 | 258 | 598 | 764.244 | 4.59 | 16 |
| 22 | DIABETES | 1020 | 358 | 300 | 599 | 772.111 | 5.49 | 18 |
| 23 | DIABETES | 945 | 258 | 100 | 547 | 649.836 | 10 | 46 |
| 24 | DIABETES | 788 | 152 | 120 | 532 | 683.088 | 11 | 45 |
| 25 | DIABETES | 759 | 163 | 184 | 587 | 760.752 | 8.27 | 16 |
| 26 | DIABETES | 840 | 189 | 198 | 514 | 661.518 | 9.47 | 18 |
| 27 | DIABETES | 845 | 167 | 174 | 597 | 705.654 | 10.24 | 21 |
| 28 | DIABETES | 901 | 176 | 162 | 520 | 666.12 | 11.26 | 23 |
| 29 | DIABETES | 897 | 185 | 132 | 600 | 773.4 | 13.25 | 32 |
| 30 | DIABETES | 864 | 197 | 213 | 620 | 737.614 | 12.64 | 28 |
| 31 | DIABETES | 826 | 145 | 248 | 573 | 727.137 | 13.478 | 29 |
| 32 | DIABETES | 845 | 165 | 264 | 610 | 780.8 | 12.2 | 26 |
| 33 | DIABETES | 710 | 125 | 258 | 598 | 764.244 | 4.59 | 16 |
| 34 | DIABETES | 842 | 358 | 300 | 599 | 772.111 | 5.49 | 18 |
| 35 | DIABETES | 924 | 258 | 100 | 547 | 649.836 | 10 | 46 |
| 36 | DIABETES | 1001 | 152 | 120 | 532 | 683.088 | 11 | 45 |
| 37 | DIABETES | 954 | 163 | 184 | 587 | 760.752 | 8.27 | 16 |
| 38 | DIABETES | 978 | 189 | 198 | 514 | 661.518 | 9.47 | 18 |
| 39 | DIABETES | 879 | 167 | 174 | 597 | 705.654 | 10.24 | 21 |
| 40 | DIABETES | 789 | 176 | 162 | 520 | 666.12 | 11.26 | 23 |
| 41 | DIABETES | 1020 | 185 | 132 | 600 | 773.4 | 13.25 | 32 |
| 42 | DIABETES | 987 | 197 | 213 | 620 | 737.614 | 12.64 | 28 |
| 43 | DIABETES | 896 | 145 | 248 | 573 | 727.137 | 13.478 | 29 |
| 44 | DIABETES | 978 | 165 | 264 | 610 | 780.8 | 12.2 | 26 |

FIG. 6H

|  | STATUS | NNmax SB | VARmax | VARmean | NNmin Standing | NNmax Standing | Tmax | Trec |
|---|---|---|---|---|---|---|---|---|
| 45 | DIABETES | 912 | 215 | 198 | 640 | 798.08 | 12.4 | 32 |
| 46 | DIABETES | 924 | 142 | 235 | 658 | 848.162 | 10.2 | 25 |
| 47 | DIABETES | 877 | 158 | 265 | 632 | 746.392 | 12 | 47 |
| 48 | DIABETES | 892 | 358 | 289 | 647 | 799.692 | 6.5 | 25 |
| 49 | DIABETES | 846 | 136 | 245 | 694 | 888.32 | 7.8 | 14 |
| 50 | DIABETES | 879 | 116 | 75.33334 | 592 | 731.12 | 14 | 50 |
| 51 | DIABETES | 800 | 216 | 157.3333 | 692 | 890.604 | 15 | 49 |
| 52 | DIABETES | 799 | 150 | 74.22222 | 516 | 609.912 | 8.112 | 28.7 |
| 53 | DIABETES | 725 | 250 | 300 | 502 | 650.592 | 14 | 48 |
| 54 | DIABETES | 769 | 169 | 290 | 545 | 702.505 | 12 | 29.1 |
| 55 | DIABETES | 789 | 178 | 270 | 584 | 689.12 | 14 | 20.4 |
| 56 | DIABETES | 748 | 245 | 310 | 597 | 762.966 | 12 | 25.5 |
| 57 | DIABETES | 762 | 187 | 190 | 587 | 744.903 | 11 | 41.1 |
| 58 | DIABETES | 697 | 450 | 222 | 578 | 743.886 | 13.5 | 20.3 |
| 59 | DIABETES | 890 | 444 | 241 | 514 | 607.548 | 13.5 | 26 |
| 60 | DIABETES | 999 | 215 | 198 | 640 | 798.08 | 12.4 | 32 |
| 61 | DIABETES | 942 | 142 | 235 | 658 | 848.162 | 10.2 | 25 |
| 62 | DIABETES | 978 | 158 | 265 | 632 | 746.392 | 12 | 47 |
| 63 | DIABETES | 936 | 358 | 289 | 647 | 799.692 | 6.5 | 25 |
| 64 | DIABETES | 941 | 136 | 245 | 694 | 888.32 | 7.8 | 14 |
| 65 | HEALTHY | 972 | 430 | 362.8571 | 524 | 821.632 | 6.032 | 12.65 |
| 66 | HEALTHY | 1060 | 432 | 390 | 580 | 927.304 | 7.78 | 33.1 |
| 67 | HEALTHY | 1016 | 387 | 373.3 | 600 | 900 | 6.5 | 12 |
| 68 | HEALTHY | 912 | 198 | 215 | 690 | 1000.5 | 10.2 | 19 |
| 69 | HEALTHY | 1015 | 265 | 298 | 700 | 1119.3 | 12.3 | 25 |
| 70 | HEALTHY | 1000 | 264 | 245 | 710 | 1104.05 | 15.4 | 21 |
| 71 | HEALTHY | 948 | 284 | 213 | 540 | 873.72 | 15 | 23 |
| 72 | HEALTHY | 845 | 298 | 129 | 789 | 1151.94 | 13.2 | 28 |
| 73 | HEALTHY | 895 | 332 | 194 | 820 | 1203.76 | 10.1 | 18 |
| 74 | HEALTHY | 869 | 386 | 182 | 520 | 809.224 | 12.36 | 25 |
| 75 | HEALTHY | 1078 | 450 | 324 | 546 | 819 | 14.25 | 21 |
| 76 | HEALTHY | 758 | 444 | 389 | 652 | 945.4 | 12.25 | 26 |
| 77 | HEALTHY | 897 | 412 | 400 | 547 | 874.653 | 10 | 12 |
| 78 | HEALTHY | 890 | 465 | 148 | 842 | 1305.942 | 10.245 | 24 |
| 79 | HEALTHY | 1005 | 478 | 234 | 700 | 1132.6 | 12.589 | 25 |
| 80 | HEALTHY | 1203 | 429 | 258 | 582 | 884.64 | 14.36 | 29 |
| 81 | HEALTHY | 945 | 412 | 247 | 664 | 1003.968 | 14.56 | 27 |
| 82 | HEALTHY | 947 | 495 | 298 | 657 | 985.5 | 11.12 | 21 |
| 83 | HEALTHY | 894 | 487 | 278 | 698 | 1081.9 | 13.45 | 23 |
| 84 | HEALTHY | 800 | 452 | 245 | 621 | 992.979 | 14.23 | 25 |
| 85 | HEALTHY | 1030 | 335 | 139 | 675 | 1047.6 | 12.1 | 19 |
| 86 | HEALTHY | 1050 | 345 | 199 | 691 | 1118.038 | 6.1 | 11 |
| 87 | HEALTHY | 1015 | 256 | 321 | 701 | 1023.46 | 12.35 | 31 |
| 88 | HEALTHY | 985 | 199 | 360 | 750 | 1155 | 14.23 | 30 |
| 89 | HEALTHY | 1026 | 326 | 260 | 710 | 1080.62 | 13.2 | 24 |

FIG. 6I

| | STATUS | NNmax SB | VARmax | VARmean | NNmin Standing | NNmax Standing | Tmax | Trec |
|---|---|---|---|---|---|---|---|---|
| 90 | HEALTHY | 895 | 333 | 241 | 760 | 1140 | 14.2 | 21 |
| 91 | HEALTHY | 947 | 302 | 299 | 754 | 1176.24 | 10.1 | 26 |
| 92 | HEALTHY | 855 | 245 | 278 | 589 | 941.811 | 9.8 | 15 |
| 93 | HEALTHY | 879 | 574 | 245 | 623 | 968.142 | 8.56 | 19 |
| 94 | HEALTHY | 984 | 458 | 265 | 547 | 885.046 | 4.56 | 18 |
| 95 | HEALTHY | 1011 | 698 | 248 | 594 | 885.06 | 9.9 | 13 |
| 96 | HEALTHY | 968 | 578 | 247 | 620 | 1003.16 | 8.97 | 17 |
| 97 | HEALTHY | 892 | 400 | 267 | 623 | 1008.014 | 7.77 | 18 |
| 98 | HEALTHY | 972 | 430 | 362.8571 | 524 | 821.632 | 6.032 | 12.65 |
| 99 | HEALTHY | 1060 | 432 | 390 | 580 | 927.304 | 7.78 | 33.1 |
| 100 | HEALTHY | 1016 | 387 | 373.3 | 600 | 900 | 6.5 | 12 |
| 101 | HEALTHY | 912 | 198 | 215 | 690 | 1000.5 | 10.2 | 19 |
| 102 | HEALTHY | 1015 | 265 | 298 | 700 | 1119.3 | 12.3 | 25 |
| 103 | HEALTHY | 1000 | 264 | 245 | 710 | 1104.05 | 15.4 | 21 |
| 104 | HEALTHY | 948 | 284 | 213 | 540 | 873.72 | 15 | 23 |
| 105 | HEALTHY | 845 | 298 | 129 | 789 | 1151.94 | 13.2 | 28 |
| 106 | HEALTHY | 895 | 332 | 194 | 820 | 1203.76 | 10.1 | 18 |
| 107 | HEALTHY | 869 | 386 | 182 | 520 | 809.224 | 12.36 | 25 |
| 108 | HEALTHY | 1078 | 450 | 324 | 546 | 819 | 14.25 | 21 |
| 109 | HEALTHY | 758 | 444 | 389 | 652 | 945.4 | 12.25 | 26 |
| 110 | HEALTHY | 897 | 412 | 400 | 547 | 874.653 | 10 | 12 |
| 111 | HEALTHY | 890 | 465 | 148 | 842 | 1305.942 | 10.245 | 24 |
| 112 | HEALTHY | 1005 | 478 | 234 | 700 | 1132.6 | 12.589 | 25 |
| 113 | HEALTHY | 1203 | 429 | 258 | 582 | 884.64 | 14.36 | 29 |
| 114 | HEALTHY | 945 | 412 | 247 | 664 | 1003.968 | 14.56 | 27 |
| 115 | HEALTHY | 947 | 495 | 298 | 657 | 985.5 | 11.12 | 21 |
| 116 | HEALTHY | 894 | 487 | 278 | 698 | 1081.9 | 13.45 | 23 |
| 117 | HEALTHY | 800 | 452 | 245 | 621 | 992.979 | 14.23 | 25 |
| 118 | HEALTHY | 1030 | 335 | 139 | 675 | 1047.6 | 12.1 | 19 |
| 119 | HEALTHY | 1050 | 345 | 199 | 691 | 1118.038 | 6.1 | 11 |
| 120 | HEALTHY | 1015 | 256 | 321 | 701 | 1023.46 | 12.35 | 31 |
| 121 | HEALTHY | 985 | 199 | 360 | 750 | 1155 | 14.23 | 30 |
| 122 | HEALTHY | 1026 | 326 | 260 | 710 | 1080.62 | 13.2 | 24 |
| 123 | HEALTHY | 895 | 333 | 241 | 760 | 1140 | 14.2 | 21 |
| 124 | HEALTHY | 947 | 302 | 299 | 754 | 1176.24 | 10.1 | 26 |
| 125 | HEALTHY | 855 | 245 | 278 | 589 | 941.811 | 9.8 | 15 |
| 126 | HEALTHY | 879 | 574 | 245 | 623 | 968.142 | 8.56 | 19 |
| 127 | HEALTHY | 984 | 458 | 265 | 547 | 885.046 | 4.56 | 18 |
| 128 | HEALTHY | 1011 | 698 | 248 | 594 | 885.06 | 9.9 | 13 |

FIG. 7A

|    | Group    | Root 1   |
|----|----------|----------|
| 1  | DIABETES | -9.3476  |
| 2  | DIABETES | -9.5232  |
| 3  | DIABETES | -10.9865 |
| 4  | DIABETES | -8.7242  |
| 5  | DIABETES | -8.5884  |
| 6  | DIABETES | -11.2693 |
| 7  | DIABETES | -9.3140  |
| 8  | DIABETES | -9.1278  |
| 9  | DIABETES | -9.0959  |
| 10 | DIABETES | -11.0725 |
| 11 | DIABETES | -9.2374  |
| 12 | DIABETES | -9.2027  |
| 13 | DIABETES | -11.5562 |
| 14 | DIABETES | -9.7996  |
| 15 | DIABETES | -9.4991  |
| 16 | DIABETES | -11.5911 |
| 17 | DIABETES | -11.1149 |
| 18 | DIABETES | -8.9963  |
| 19 | DIABETES | -8.8818  |
| 20 | DIABETES | -11.1577 |
| 21 | DIABETES | -9.1943  |
| 22 | DIABETES | -9.0558  |
| 23 | DIABETES | -11.4325 |
| 24 | DIABETES | -9.0223  |
| 25 | DIABETES | -8.5841  |
| 26 | DIABETES | -8.6345  |
| 27 | DIABETES | -11.3819 |
| 28 | DIABETES | -9.0559  |
| 29 | DIABETES | -9.0454  |
| 30 | DIABETES | -11.4657 |
| 31 | DIABETES | -9.1082  |
| 32 | DIABETES | -10.3832 |
| 33 | DIABETES | -10.7665 |
| 34 | DIABETES | -9.1357  |
| 35 | DIABETES | -8.6845  |
| 36 | DIABETES | -7.6954  |
| 37 | DIABETES | -10.8222 |
| 38 | DIABETES | -9.0884  |
| 39 | DIABETES | -11.3924 |
| 40 | DIABETES | -9.1799  |
| 41 | DIABETES | -11.0873 |

FIG. 7B

| 42 | DIABETES | -8.2295 |
|---|---|---|
| 43 | DIABETES | -6.4428 |
| 44 | DIABETES | -7.1334 |
| 45 | DIABETES | -11.1983 |
| 46 | DIABETES | -9.2538 |
| 47 | DIABETES | -10.1610 |
| 48 | DIABETES | -8.4712 |
| 49 | DIABETES | -8.2188 |
| 50 | DIABETES | -8.8990 |
| 51 | DIABETES | -11.4934 |
| 52 | DIABETES | -11.6011 |
| 53 | DIABETES | -10.5907 |
| 54 | DIABETES | -12.2495 |
| 55 | DIABETES | -10.4093 |
| 56 | DIABETES | -10.1302 |
| 57 | DIABETES | -8.7694 |
| 58 | DIABETES | -9.2478 |
| 59 | DIABETES | -9.8326 |
| 60 | DIABETES | -9.6406 |
| 61 | DIABETES | -11.9578 |
| 62 | DIABETES | -12.1825 |
| 63 | DIABETES | -8.8980 |
| 64 | DIABETES | -9.0345 |
| 65 | HEALTHY | 9.6250 |
| 66 | HEALTHY | 9.5341 |
| 67 | HEALTHY | 8.9414 |
| 68 | HEALTHY | 9.0173 |
| 69 | HEALTHY | 10.2362 |
| 70 | HEALTHY | 10.5067 |
| 71 | HEALTHY | 8.7871 |
| 72 | HEALTHY | 10.0172 |
| 73 | HEALTHY | 9.2227 |
| 74 | HEALTHY | 9.3548 |
| 75 | HEALTHY | 9.7580 |
| 76 | HEALTHY | 9.9200 |
| 77 | HEALTHY | 9.3763 |
| 78 | HEALTHY | 9.2069 |
| 79 | HEALTHY | 10.4042 |
| 80 | HEALTHY | 10.2012 |
| 81 | HEALTHY | 8.8216 |
| 82 | HEALTHY | 9.7322 |
| 83 | HEALTHY | 11.3844 |

FIG. 7C

| 84 | HEALTHY | 9.7765 |
|---|---|---|
| 85 | HEALTHY | 10.2588 |
| 86 | HEALTHY | 9.5954 |
| 87 | HEALTHY | 9.7588 |
| 88 | HEALTHY | 9.8602 |
| 89 | HEALTHY | 9.5577 |
| 90 | HEALTHY | 10.0677 |
| 91 | HEALTHY | 9.5621 |
| 92 | HEALTHY | 10.4281 |
| 93 | HEALTHY | 11.0545 |
| 94 | HEALTHY | 9.3259 |
| 95 | HEALTHY | 10.0612 |
| 96 | HEALTHY | 10.3474 |
| 97 | HEALTHY | 9.2923 |
| 98 | HEALTHY | 9.6250 |
| 99 | HEALTHY | 9.5341 |
| 100 | HEALTHY | 8.9414 |
| 101 | HEALTHY | 9.0173 |
| 102 | HEALTHY | 10.2362 |
| 103 | HEALTHY | 10.5067 |
| 104 | HEALTHY | 8.7871 |
| 105 | HEALTHY | 10.0172 |
| 106 | HEALTHY | 9.2227 |
| 107 | HEALTHY | 9.3548 |
| 108 | HEALTHY | 9.7580 |
| 109 | HEALTHY | 9.9200 |
| 110 | HEALTHY | 9.3763 |
| 111 | HEALTHY | 9.2069 |
| 112 | HEALTHY | 10.4042 |
| 113 | HEALTHY | 10.2012 |
| 114 | HEALTHY | 8.8216 |
| 115 | HEALTHY | 9.7322 |
| 116 | HEALTHY | 11.3844 |
| 117 | HEALTHY | 9.7765 |
| 118 | HEALTHY | 10.2588 |
| 119 | HEALTHY | 9.5954 |
| 120 | HEALTHY | 9.7588 |
| 121 | HEALTHY | 9.8602 |
| 122 | HEALTHY | 9.5577 |
| 123 | HEALTHY | 10.0677 |
| 124 | HEALTHY | 9.5621 |
| 125 | HEALTHY | 10.4281 |

FIG. 7D

| 126 | HEALTHY | 11.0545 |
|-----|---------|---------|
| 127 | HEALTHY | 9.3259  |
| 128 | HEALTHY | 10.0612 |

| STATUS | E/I Ratio | SD | RMS-SD | TP | 30:15 Ratio | NNmin SB | NNmin Standing | NNmax Standing |
|---|---|---|---|---|---|---|---|---|
| 1 DIABETES 1 | 1.1075 | 31.48 | 27.51 | 63.64 | 1.083 | 572 | 372 | 592 |
| 2 HEALTHY | 1.3966 | 110.76 | 52.63 | 1020.37 | 1.349 | 748 | 620 | 936 |
Figure 8: Test results for two exemplar patients.
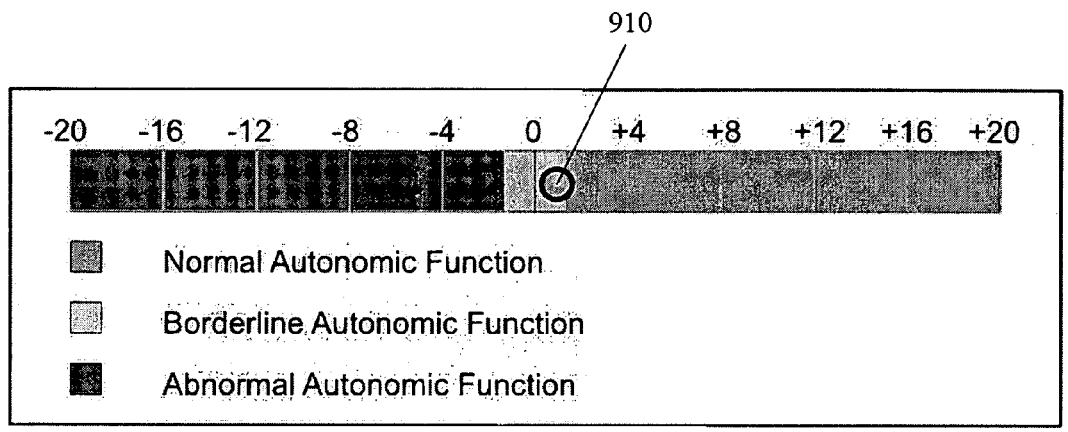
Figure 9: Exemplar graphical display of autonomic ranking for exemplar Patient2.

Initial test values:
Minimum threshold (minTHR) = 0
Maximum threshold (maxTHR) = maximum possible X value (ECG signal)
Minimum confirmation period (minCP) = 333 ms
Maximum confirmation period (maxCP) = 2000 ms

FIG. 14A

| | STATUS | RMS-SD | TP | E/I Ratio | SD | 30:15 Ratio | NNmin SB | NNmin Standing | NNmax Standing |
|---|---|---|---|---|---|---|---|---|---|
| 1 | DIABETES | 50.93 | 380.94 | 1.1889 | 62.12 | 1.235 | 616 | 592 | 731.12 |
| 2 | DIABETES | 58.039 | 389 | 1.239 | 56.41 | 1.287 | 796 | 692 | 890.604 |
| 3 | DIABETES | 10.065 | 181.622 | 1.116 | 35.25 | 1.182 | 532 | 516 | 609.912 |
| 4 | DIABETES | 52.93 | 382.94 | 1.19 | 62.15 | 1.296 | 600 | 502 | 650.592 |
| 5 | DIABETES | 60.039 | 400 | 1.24 | 58 | 1.289 | 580 | 545 | 702.505 |
| 6 | DIABETES | 10.07 | 182 | 1.116 | 35.3 | 1.18 | 550 | 584 | 689.12 |
| 7 | DIABETES | 51.93 | 598 | 1.18 | 62 | 1.278 | 700 | 597 | 762.966 |
| 8 | DIABETES | 51.9 | 687 | 1.1889 | 62.12 | 1.269 | 730 | 587 | 744.903 |
| 9 | DIABETES | 58 | 220 | 1.239 | 56.41 | 1.287 | 680 | 578 | 743.886 |
| 10 | DIABETES | 10.065 | 182.678 | 1.116 | 35.25 | 1.182 | 578 | 514 | 607.548 |
| 11 | DIABETES | 52.93 | 648 | 1.19 | 62.15 | 1.247 | 592 | 640 | 798.08 |
| 12 | DIABETES | 60.039 | 247 | 1.24 | 58 | 1.289 | 658 | 658 | 848.162 |
| 13 | DIABETES | 10.07 | 182 | 1.116 | 35.3 | 1.181 | 612 | 632 | 746.392 |
| 14 | DIABETES | 51.93 | 378 | 1.18 | 62 | 1.236 | 623 | 647 | 799.692 |
| 15 | DIABETES | 59 | 268 | 1.22 | 61 | 1.28 | 684 | 694 | 888.32 |
| 16 | DIABETES | 10 | 181 | 1.114 | 35 | 1.18 | 724 | 555 | 654.9 |
| 17 | DIABETES | 11 | 182 | 1.125 | 36 | 1.188 | 689 | 532 | 632.016 |
| 18 | DIABETES | 51.91 | 770 | 1.1889 | 62.12 | 1.245 | 678 | 547 | 681.015 |
| 19 | DIABETES | 59 | 381 | 1.239 | 56.41 | 1.287 | 625 | 568 | 731.016 |
| 20 | DIABETES | 10.065 | 184.678 | 1.116 | 35.25 | 1.182 | 624 | 512 | 605.184 |
| 21 | DIABETES | 52.93 | 299 | 1.19 | 62.15 | 1.278 | 599 | 598 | 764.244 |
| 22 | DIABETES | 60.039 | 384 | 1.24 | 58 | 1.289 | 726 | 599 | 772.111 |
| 23 | DIABETES | 10.07 | 182 | 1.116 | 35.3 | 1.188 | 720 | 547 | 649.836 |
| 24 | DIABETES | 51.93 | 378 | 1.18 | 62 | 1.284 | 580 | 532 | 683.088 |
| 25 | DIABETES | 51.94 | 780 | 1.1889 | 62.12 | 1.296 | 594 | 587 | 760.752 |
| 26 | DIABETES | 59.1 | 380 | 1.239 | 56.41 | 1.287 | 577 | 514 | 661.518 |
| 27 | DIABETES | 10.065 | 182.6 | 1.116 | 35.25 | 1.182 | 588 | 597 | 705.654 |
| 28 | DIABETES | 52.93 | 278 | 1.19 | 62.15 | 1.281 | 645 | 520 | 666.12 |
| 29 | DIABETES | 60.039 | 155 | 1.24 | 58 | 1.289 | 625 | 600 | 773.4 |
| 30 | DIABETES | 10.07 | 182 | 1.116 | 35.3 | 1.1897 | 619 | 620 | 737.614 |
| 31 | DIABETES | 51.93 | 794 | 1.18 | 62 | 1.269 | 684 | 573 | 727.137 |
| 32 | DIABETES | 59 | 382 | 1.223 | 47 | 1.28 | 675 | 610 | 780.8 |
| 33 | DIABETES | 25.25 | 379 | 1.123 | 45.23 | 1.189 | 600 | 598 | 764.244 |
| 34 | DIABETES | 43.15 | 389 | 1.234 | 51.23 | 1.126 | 610 | 599 | 772.111 |
| 35 | DIABETES | 35.12 | 181 | 1.156 | 65.52 | 1.299 | 620 | 547 | 649.836 |
| 36 | DIABETES | 45.18 | 380 | 1.22 | 64.25 | 1.264 | 630 | 532 | 683.088 |
| 37 | DIABETES | 54.78 | 405 | 1.17 | 55.55 | 1.185 | 740 | 587 | 760.752 |
| 38 | DIABETES | 32.12 | 190 | 1.18 | 54.12 | 1.234 | 720 | 514 | 661.518 |
| 39 | DIABETES | 22.16 | 600 | 1.15 | 32.32 | 1.2 | 654 | 597 | 705.654 |
| 40 | DIABETES | 24.26 | 700 | 1.19 | 39.34 | 1.211 | 586 | 520 | 666.12 |
| 41 | DIABETES | 28.46 | 230 | 1.14 | 41.02 | 1.236 | 687 | 600 | 773.4 |
| 42 | DIABETES | 27.98 | 184 | 1.187 | 63.25 | 1.245 | 623 | 620 | 737.614 |
| 43 | DIABETES | 45.56 | 650 | 1.244 | 71.25 | 1.281 | 642 | 573 | 727.137 |
| 44 | DIABETES | 35.46 | 250 | 1.211 | 70.02 | 1.263 | 649 | 610 | 780.8 |

FIG. 14B

|    | STATUS | RMS-SD | TP | E/I Ratio | SD | 30:15 Ratio | NNmin SB | NNmin Standing | NNmax Standing |
|---|---|---|---|---|---|---|---|---|---|
| 45 | DIABETES | 37.48 | 190 | 1.201 | 34.56 | 1.245 | 687 | 640 | 798.08 |
| 46 | DIABETES | 35.24 | 389 | 1.222 | 45.12 | 1.278 | 702 | 658 | 848.162 |
| 47 | DIABETES | 33.25 | 267 | 1.189 | 47.18 | 1.256 | 711 | 632 | 746.392 |
| 48 | DIABETES | 21.24 | 182 | 1.245 | 43.26 | 1.212 | 623 | 647 | 799.692 |
| 49 | DIABETES | 20.21 | 182 | 1.248 | 43.46 | 1.246 | 645 | 694 | 888.32 |
| 50 | DIABETES | 36.38 | 779 | 1.188 | 55.23 | 1.239 | 690 | 592 | 731.12 |
| 51 | DIABETES | 47.56 | 390 | 1.177 | 41.95 | 1.248 | 689 | 692 | 890.604 |
| 52 | DIABETES | 35.47 | 187 | 1.165 | 33.28 | 1.284 | 674 | 516 | 609.912 |
| 53 | DIABETES | 24.22 | 320 | 1.128 | 39.15 | 1.264 | 598 | 502 | 650.592 |
| 54 | DIABETES | 54.24 | 398 | 1.1364 | 41.23 | 1.234 | 578 | 545 | 702.505 |
| 55 | DIABETES | 51.2 | 399 | 1.211 | 45.11 | 1.245 | 534 | 584 | 689.12 |
| 56 | DIABETES | 47.45 | 350 | 1.239 | 36.31 | 1.284 | 596 | 597 | 762.966 |
| 57 | DIABETES | 24.35 | 790 | 1.237 | 32.15 | 1.267 | 578 | 587 | 744.903 |
| 58 | DIABETES | 24.26 | 394 | 1.235 | 31.24 | 1.234 | 569 | 578 | 743.886 |
| 59 | DIABETES | 27.28 | 200 | 1.236 | 30.12 | 1.247 | 610 | 514 | 607.548 |
| 60 | DIABETES | 27.39 | 230 | 1.237 | 34.69 | 1.236 | 623 | 640 | 798.08 |
| 61 | DIABETES | 31.29 | 190 | 1.122 | 38.15 | 1.248 | 627 | 658 | 848.162 |
| 62 | DIABETES | 31.89 | 185 | 1.126 | 39.12 | 1.239 | 638 | 632 | 746.392 |
| 63 | DIABETES | 32.56 | 845 | 1.238 | 41.32 | 1.247 | 659 | 647 | 799.692 |
| 64 | DIABETES | 33.46 | 425 | 1.24 | 41.36 | 1.294 | 645 | 694 | 888.32 |
| 65 | HEALTHY | 119.14 | 2300 | 1.68 | 153.9755 | 1.568 | 650 | 524 | 821.632 |
| 66 | HEALTHY | 120 | 2000 | 1.681 | 153.8888 | 1.5988 | 620 | 580 | 927.304 |
| 67 | HEALTHY | 63.34 | 1500.03 | 1.603 | 138.509 | 1.5 | 556 | 600 | 900 |
| 68 | HEALTHY | 86.78 | 3331.34 | 1.62 | 141.3 | 1.45 | 600 | 690 | 1000.5 |
| 69 | HEALTHY | 121 | 2589 | 1.688 | 154 | 1.599 | 500 | 700 | 1119.3 |
| 70 | HEALTHY | 65 | 3244 | 1.62 | 139 | 1.555 | 777 | 710 | 1104.05 |
| 71 | HEALTHY | 125 | 2999 | 1.611 | 158 | 1.618 | 775 | 540 | 873.72 |
| 72 | HEALTHY | 70.8 | 3400 | 1.59 | 152 | 1.46 | 745 | 789 | 1151.94 |
| 73 | HEALTHY | 70.7 | 2498.7 | 1.57 | 151 | 1.468 | 510 | 820 | 1203.76 |
| 74 | HEALTHY | 119.18 | 1902.56 | 1.685 | 153.8812 | 1.5562 | 630 | 520 | 809.224 |
| 75 | HEALTHY | 63.34 | 2500 | 1.603 | 138.509 | 1.5 | 614 | 546 | 819 |
| 76 | HEALTHY | 86.78 | 3331.34 | 1.65 | 141.3 | 1.45 | 514 | 652 | 945.4 |
| 77 | HEALTHY | 126 | 2456 | 1.688 | 154 | 1.599 | 800 | 547 | 874.653 |
| 78 | HEALTHY | 65 | 2220 | 1.62 | 135 | 1.551 | 700 | 842 | 1305.942 |
| 79 | HEALTHY | 121 | 3125 | 1.611 | 170 | 1.618 | 625 | 700 | 1132.6 |
| 80 | HEALTHY | 70.8 | 2400 | 1.59 | 152 | 1.52 | 645 | 582 | 884.64 |
| 81 | HEALTHY | 119.111 | 1902.56 | 1.689 | 153.9456 | 1.512 | 678 | 664 | 1003.968 |
| 82 | HEALTHY | 63.34 | 2899 | 1.603 | 138.509 | 1.5 | 698 | 657 | 985.5 |
| 83 | HEALTHY | 86.78 | 3331.34 | 1.7 | 141.3 | 1.55 | 659 | 698 | 1081.9 |
| 84 | HEALTHY | 128 | 2698 | 1.688 | 154 | 1.599 | 600 | 621 | 992.979 |
| 85 | HEALTHY | 65 | 2487 | 1.62 | 140 | 1.552 | 645 | 675 | 1047.6 |
| 86 | HEALTHY | 129 | 2789 | 1.611 | 171 | 1.618 | 687 | 691 | 1118.038 |
| 87 | HEALTHY | 70.8 | 2777 | 1.59 | 152 | 1.46 | 698 | 701 | 1023.46 |
| 88 | HEALTHY | 70.7 | 2498.7 | 1.57 | 152 | 1.54 | 589 | 750 | 1155 |
| 89 | HEALTHY | 119.119 | 2902.35 | 1.675 | 153.9999 | 1.522 | 584 | 710 | 1080.62 |

FIG. 14C

|     | STATUS  | RMS-SD  | TP      | E/I Ratio | SD       | 30:15 Ratio | NNmin SB | NNmin Standing | NNmax Standing |
|-----|---------|---------|---------|-----------|----------|-------------|----------|----------------|----------------|
| 90  | HEALTHY | 63.34   | 3458.59 | 1.603     | 138.509  | 1.5         | 678      | 760            | 1140           |
| 91  | HEALTHY | 86.78   | 3331.34 | 1.61      | 141.3    | 1.56        | 594      | 754            | 1176.24        |
| 92  | HEALTHY | 119     | 2945.36 | 1.688     | 154      | 1.599       | 678      | 589            | 941.811        |
| 93  | HEALTHY | 65      | 3215.25 | 1.62      | 141      | 1.554       | 645      | 623            | 968.142        |
| 94  | HEALTHY | 122.356 | 3000.02 | 1.611     | 159      | 1.618       | 635      | 547            | 885.046        |
| 95  | HEALTHY | 70.8    | 2400    | 1.59      | 152      | 1.49        | 600      | 594            | 885.06         |
| 96  | HEALTHY | 121     | 4056    | 1.611     | 160      | 1.618       | 620      | 620            | 1003.16        |
| 97  | HEALTHY | 121     | 2932.569| 1.611     | 158      | 1.618       | 580      | 623            | 1008.014       |
| 98  | HEALTHY | 119.14  | 2300    | 1.68      | 153.9755 | 1.568       | 650      | 524            | 821.632        |
| 99  | HEALTHY | 120     | 2000    | 1.681     | 153.8888 | 1.5988      | 620      | 580            | 927.304        |
| 100 | HEALTHY | 63.34   | 1500.03 | 1.603     | 138.509  | 1.5         | 556      | 600            | 900            |
| 101 | HEALTHY | 86.78   | 3331.34 | 1.62      | 141.3    | 1.45        | 600      | 690            | 1000.5         |
| 102 | HEALTHY | 121     | 2589    | 1.688     | 154      | 1.599       | 500      | 700            | 1119.3         |
| 103 | HEALTHY | 65      | 3244    | 1.62      | 139      | 1.555       | 777      | 710            | 1104.05        |
| 104 | HEALTHY | 125     | 2999    | 1.611     | 158      | 1.618       | 775      | 540            | 873.72         |
| 105 | HEALTHY | 70.8    | 3400    | 1.59      | 152      | 1.46        | 745      | 789            | 1151.94        |
| 106 | HEALTHY | 70.7    | 2498.7  | 1.57      | 151      | 1.468       | 510      | 820            | 1203.76        |
| 107 | HEALTHY | 119.18  | 1902.56 | 1.685     | 153.8812 | 1.5562      | 630      | 520            | 809.224        |
| 108 | HEALTHY | 63.34   | 2500    | 1.603     | 138.509  | 1.5         | 614      | 546            | 819            |
| 109 | HEALTHY | 86.78   | 3331.34 | 1.65      | 141.3    | 1.45        | 514      | 652            | 945.4          |
| 110 | HEALTHY | 126     | 2456    | 1.688     | 154      | 1.599       | 800      | 547            | 874.653        |
| 111 | HEALTHY | 65      | 2220    | 1.62      | 135      | 1.551       | 700      | 842            | 1305.942       |
| 112 | HEALTHY | 121     | 3125    | 1.611     | 170      | 1.618       | 625      | 700            | 1132.6         |
| 113 | HEALTHY | 70.8    | 2400    | 1.59      | 152      | 1.52        | 645      | 582            | 884.64         |
| 114 | HEALTHY | 119.111 | 1902.56 | 1.689     | 153.9456 | 1.512       | 678      | 664            | 1003.968       |
| 115 | HEALTHY | 63.34   | 2899    | 1.603     | 138.509  | 1.5         | 698      | 657            | 985.5          |
| 116 | HEALTHY | 86.78   | 3331.34 | 1.7       | 141.3    | 1.55        | 659      | 698            | 1081.9         |
| 117 | HEALTHY | 128     | 2698    | 1.688     | 154      | 1.599       | 600      | 621            | 992.979        |
| 118 | HEALTHY | 65      | 2487    | 1.62      | 140      | 1.552       | 645      | 675            | 1047.6         |
| 119 | HEALTHY | 129     | 2789    | 1.611     | 171      | 1.618       | 687      | 691            | 1118.038       |
| 120 | HEALTHY | 70.8    | 2777    | 1.59      | 152      | 1.46        | 698      | 701            | 1023.46        |
| 121 | HEALTHY | 70.7    | 2498.7  | 1.57      | 152      | 1.54        | 589      | 750            | 1155           |
| 122 | HEALTHY | 119.119 | 2902.35 | 1.675     | 153.9999 | 1.522       | 584      | 710            | 1080.62        |
| 123 | HEALTHY | 63.34   | 3458.59 | 1.603     | 138.509  | 1.5         | 678      | 760            | 1140           |
| 124 | HEALTHY | 86.78   | 3331.34 | 1.61      | 141.3    | 1.56        | 594      | 754            | 1176.24        |
| 125 | HEALTHY | 119     | 2945.36 | 1.688     | 154      | 1.599       | 678      | 589            | 941.811        |
| 126 | HEALTHY | 65      | 3215.25 | 1.62      | 141      | 1.554       | 645      | 623            | 968.142        |
| 127 | HEALTHY | 122.356 | 3000.02 | 1.611     | 159      | 1.618       | 635      | 547            | 885.046        |
| 128 | HEALTHY | 70.8    | 2400    | 1.59      | 152      | 1.49        | 600      | 594            | 885.06         |

Fig. 15B

| N-1 | t |
|---|---|
| 5 | 3.04 |
| 6 | 2.78 |
| 7 | 2.62 |
| 8 | 2.51 |
| 9 | 2.43 |
| 10 | 2.37 |
| 11 | 2.33 |
| 12 | 2.29 |
| 13 | 2.26 |
| 14 | 2.24 |
| 15 | 2.22 |
| 16 | 2.20 |
| 17 | 2.18 |
| 18 | 2.17 |
| 20 | 2.145 |
| 25 | 2.105 |
| 30 | 2.079 |
| 35 | 2.061 |
| 40 | 2.048 |
| 45 | 2.038 |
| 50 | 2.030 |
| 60 | 2.018 |
| 70 | 2.009 |
| 80 | 2.003 |
| 90 | 1.998 |
| 100 | 1.994 |
| 1000 | 1.960 |

FIG. 16A

|   | Parameter Name | HRV Test | Description |
|---|---|---|---|
| 1 | 30:15 Ratio | Orthostatic | 30:15 Ratio (ratio between the maximum HR recording during the first 15 seconds of standing to the minimum HR recorded during first 30 seconds of standing) |
| 2 | NNmin Standing | Orthostatic | Minimum NN (ms) |
| 3 | NNmax Standing | Orthostatic | Maximum NN (ms) |
| 4 | Tmax | Orthostatic | Time to achieve maximum HR after standing up (ms) |
| 5 | Trec | Orthostatic | Time to recover HR to 75% of its baseline level (ms) |

FIG. 16B

|   | Parameter Name | HRV Test | Description |
|---|---|---|---|
| 1 | E/I Ratio | Slow Metronomic Breathing | Mean ratio of HR max/HR min in each consecutive breath cycle (also known as E/I Ratio) |
| 2 | SD | Slow Metronomic Breathing | Standard deviation of NN intervals |
| 3 | NNmin SB | Slow Metronomic Breathing | Minimum NN (ms) |
| 4 | NNmax SB | Slow Metronomic Breathing | Maximum NN (ms) |
| 5 | VARmax | Slow Metronomic Breathing | Maximum Variance of NN between consecutive breath cycles |
| 6 | VARmean | Slow Metronomic Breathing | Mean Variance of NN between consecutive breath cycles |

FIG. 16C

|   | Parameter Name | HRV Test | Description |
|---|---|---|---|
| 1 | RMS-SD | Short-term resting HRV | Root mean square of the differences in successive NN intervals |
| 2 | NN | Short-term resting HRV | Mean NN interval (NN) |
| 3 | SDNN | Short-term resting HRV | Standard deviation of NN intervals |

FIG. 16D

|   | Parameter Name | HRV Test | Description |
|---|---|---|---|
| 1 | TP | Short-term resting HRV | Power spectrum for a fourth frequency range that comprises the first predetermined frequency range, the second predetermined frequency range and the third predetermined frequency range |
| 2 | LFnorm | Short-term resting HRV | (LF):(TP-VLF) ratio |
| 3 | HFnorm | Short-term resting HRV | (HF):(TP-VLF) ratio |
| 4 | LF/HF | Short-term resting HRV | LF:HF ratio |
| 5 | VLF | Short-term resting HRV | Power spectrum for a first predetermined frequency range |
| 6 | LF | Short-term resting HRV | Power spectrum for a second predetermined frequency range |
| 7 | HF | Short-term resting HRV | Power spectrum for a third predetermined frequency range |

METHOD AND APPARATUS FOR DETECTING PHYSIOLOGIC SIGNALS

CROSS-REFERENCE TO RELATED APPLICATIONS

This application is a continuation of U.S. patent application, Ser. No. 10/842,294, entitled "Method and apparatus for measurement of autonomic nervous system function", filed on May 10, 2004, now abandoned which is hereby incorporated by reference.

BACKGROUND INFORMATION

1. Technical Field

The present invention relates to apparatuses and methods for detecting physiological signals.

2. Description of the Related Art

The autonomic nervous system (ANS) is primarily responsible for the fine-tuned regulation of many human organs and systems. An individual whose autonomic nervous system, correctly regulates such organs and systems is said to have good autonomic function. Improper autonomic function may be referred to as autonomic dysfunction, which can be the result of autonomic neuropathy (AN). AN can result in improper regulation of organs and systems, which in turn may lead to the malfunction of those organs and systems. AN is often associated with a number of disorders such as diabetes and coronary artery disease. In fact, the last two decades have witnessed the recognition of a significant relationship between AN and cardiovascular mortality, including sudden cardiac death. Thus, testing for AN may be a useful health monitoring tool.

One way to test for AN is by evaluating how well the ANS regulates the heart through a "heart rate variability" (HRV) study. In such a study, a patient performs certain breathing tests, which, in a person with a properly functioning ANS, will cause fluctuations in the patient's heart rate (HR). As AN increases HRV decreases. HRV is a measurement of the fluctuation of R-R intervals in a patient's electrocardiogram (ECG). The R-R interval is the distance between R peaks in a QRS complex. Detection of R-R intervals may be achieved by various methods such as a simple threshold technique or statistical method, both of which are known to those of ordinary skill in the art.

HRV testing is useful for more than determining whether a patient has AN. For example, HRV testing may be used to monitor disease progression as a function of changes in autonomic function. HRV testing may also be used to evaluate a patient's response to a prescribed treatment for an autonomic disorder. Other applications for HRV testing include: general health screening, diabetic neuropathy assessment, pre-condition cardiac health screening, post-myocardial infarction risk assessment and evaluation, drug studies including the relationship between certain drug dosages and AN function, and stress measurement of, for example, ADHD children.

Several clinical tests, known to those of ordinary skill in the art, help physicians or clinicians measure HRV. Examples of such tests are the Slow Metronomic Breathing test, Valsalva test and Orthostatic test. Each test measures certain HRV parameters, subsets of which may indicate whether a patient is predisposed for, or afflicted with, AN and one or more of its related maladies such as diabetes. These three tests will now be addressed.

1. Slow Metronomic Breathing Test

The Slow Metronomic Breathing test is designed to assess the parasympathetic branch of the ANS. As those of ordinary skill in the art will appreciate, during the test the patient breathes deeply and evenly, in a supine position, at six breaths per minute. Any events that could alter spontaneous breathing, such as speech or coughing, should be limited. To foster patient compliance with the prescribed breathing regimen, the patient should breathe for one minute following pacer movements, similar to a metronome, which may be displayed on a computer screen.

The breathing regimen described above helps assess ANS function because parasympathetic regulation of the heart rhythm relies on different types of receptors located in the lungs. These receptors are taxed by the deep breathing performed during the Metronomic test. More specifically, chemoreceptors detect concentrations of $CO_2$ and H+ ions in the arterial blood, which change as one breathes. Chemoreceptors send signals to the brain that are representative of the concentration of these elements. The brain may then regulate the heart, by adjusting the heart rate, to achieve these reported concentration levels. Mechanoreceptors, unlike chemoreceptors, react to changes of air pressure within a patient's airways. Breathing, and especially heavy breathing, creates changes in intrathoracic pressure which are then sensed by mechanoreceptors. This results in a change in blood pressure. The baroreflex mechanism then causes changes in heart rate. These changes in pressure produce signals that are sent along afferent fibers from the mechanoreceptors to the brain stem. In summary, changes in breathing can affect both chemoreceptors and mechanoreceptors, both located in the lungs, which in turn communicate with the brain to potentially illicit a change in HR for a person with "good HRV."

The HRV parameters or measurements in measured in the Metronomic test may include one or more of the measurements found in FIG. 16B. The parameters are calculated on "normal-to-normal" inter-beat intervals (NN intervals), which are R-R intervals calculated on beats caused by normal heart contractions paced by sinus node depolarization.

2. The Orthostatic Test

Like the Metronomic test, the Othostatic test is used to evaluate the effect of parasympathetic regulation on HR. Therefore, the test provides a good indication of autonomic function and HRV. More specifically, the Orthostatic test evaluates how a change in body position affects heart rate. The patient is instructed to lie down in an idle, relaxed, supine position. After a minute of recording ECG signals, the patient stands up while avoiding any rapid movements. The patient remains standing for another minute. The patient's heart rhythm is monitored continuously while the patient lies down and stands up. HR monitoring should continue until a stationary state in HR is detected.

The Orthostatic test helps evaluate autonomic function because it taxes a set of regulatory mechanisms that support parasympathetic regulation of the heart rhythm. More specifically, blood mass redistribution takes place when a patient changes from a supine position to a standing position. The baroreceptors situated in the aortic arch and carotid nodes perceive this change in blood distribution and communicate the change to the brain via afferent fibers. These communications cause an increase in the activation of sympathetic efferent fibers and a decrease in activation of parasympathetic efferent fibers. These efferent fibers then transmit regulatory instructions from the brain down the sympathetic and parasympathetic nerves pathways. The tonus of the arteries in the carotid sinus is consequently decreased causing activation of the adrenergic receptors of blood vessel walls and perivascular tissues. Thus, the body shift causes a sympathetic positive chronotropic effect. Concurrently, when the patient changes positions, an increase of muscular activity takes place thereby causing an increase in blood delivery from the extremities. The sympathetic effects are increased and sustained during the post-stimuli period to support the vertical posture. So, blood pressure gradually increases due to activation of the sympathetic NS. The increase in blood pressure causes stimulation of the parasympathetic NS. This stimulation occurs via the baroreflex mechanism and is followed by a decrease in HR. In summary, changing positions taxes the ANS, which should result in a change in heart rate for those patients with good HRV.

The HRV parameters or measurements measured in the Metronomic test may include one or more of the measurements found in FIG. 16A. The parameters are calculated on "normal-to-normal" inter-beat intervals (NN intervals), which are R-R intervals calculated on beats caused by normal heart contractions paced by sinus node depolarization.

3. The Valsalva Test

The Valsalva test also helps assess autonomic function. The Valsalva test commences with the patient in the supine position with his head slightly elevated. The patient then strains by blowing into a mouthpiece until a 40 mm Hg pressure is obtained for 15 seconds. Following cessation of the Valsalva strain, the patient relaxes and breathes at a normal rate. The ECG is monitored during the strain and at 30-45 seconds afterwards. Maximum and minimum heart rates are obtained respectively at about one second after cessation of strain and then 15-20 seconds later. This process is repeated three times and the largest heart rate ratio is considered the best reflection of autonomic function. The end result of the test is a measurement called the Valsalva ratio. The Valsalva ratio ("VR"), which constitutes a HRV parameter, is the ratio of the longest R-R interval to the shortest R-R interval at one second and 15-20 seconds after the Valsalva maneuver is completed. Again, the methods for performing the Metronomic, Orthostatic and Valsalva tests are known to those of ordinary skill in the art.

While the methods for performing the Metronomic, Orthostatic and Valsalva tests produce valuable information regarding autonomic function, prior art methods and equipment fail to take full advantage of the available information. For instance, in the prior art, normative databases for HRV values are not created and maintained. As an illustration, the prior art does not attempt to determine normal VARmax values for patients according to such diverse factors as race, age, smoking history and gender. Consequently, the VARmax value of a black, 30-year old, non-smoking man is often compared with that of a 30-year old, white woman who has smoked for 10 years. Doing so may lead to an inaccurate assessment of the male patient's autonomic function. Furthermore, the prior art does not attempt to link certain factors such as race, age and VARmax value with a risk factor for contracting, for example, hypertension. An additional limitation in the prior art is the inability to provide normative databases that expand, and whose accuracy is refined as HRV studies continue to be performed. Finally, the prior art requires expensive, complicated and burdensome HRV testing equipment that many non-specialists are unlikely to use. As a result, AN associated maladies, such as heart disease and diabetes, are not assessed as well as possible because the vast majority of clinicians do not possess these complex tools.

Therefore, a method and apparatus for measuring autonomic nervous system function is needed that can help patients gain early notice when they are at risk for developing an illness forecasted or indicated by poor autonomic function. In addition, a need exists for specific normative databases that provide targeted HRV information that focuses on both demographic and health factors. Such a normative database should help discern HRV patterns to allow clinicians to better assess potential health issues for patients. The normative database should continue to expand and provide more valuable forecasting and assessment tools as HRV studies are conducted over time. Finally, a need exists for HRV testing which is available through an Application Service Provider model so practitioners need not invest heavily in sophisticated equipment that must be updated regularly. Such testing capabilities would become a powerful tool in the clinician's hands for early detection of various medical problems before those maladies show any clinical manifestation. Furthermore, such capabilities would better allow health care providers to assess progress or deterioration in a patient's previously assessed autonomic dysfunction.

SUMMARY DESCRIPTION

In one embodiment of the invention, background data from a population of patients is obtained. The population of patients may be comprised of patients with both normal and abnormal autonomic function. Then, the invention may receive ECG data from the same population of patients. HRV parameters such as NNmin SB and SD may be measured from the ECG data. Afterwards, discriminant analysis may be performed on the HRV parameters and background data to determine discriminant equations, wherein each discriminant equation discriminates between patients with normal and abnormal autonomic function. For instance, patterns may be identified whereby certain HRV parameter measurements, when combined with certain background information, such as race and gender, may distinguish between individuals with early signs of diabetes and those without such signs. After these equations are developed, new patients may be tested. Each new patient provides background data and HRV data. Then, the invention may select, from among the discriminant equations it has previously developed from the data from the population of patients, only those equations that pertain to the particular patient being tested. Consequently, data from a 20 year old black woman may be compared to other 20 year old black women, each afflicted with a different malady. The new patient's HRV data could then be input into the selected equations to provide autonomic rankings that are indicative of the new patient's autonomic function. In one embodiment of the invention, the background and HRV data from each new patient may be added to the same information that exists for the population of patients thereby creating increasingly larger normative data sets from which future patients' autonomic function can be more accurately assessed.

In an alternative embodiment of the invention, a method for assessing autonomic performance concerns an application for storing a population data set on a server. The population data set may be comprised of physiologic data and background data received from a population of patients wherein the population of patients is comprised of patients with abnormal autonomic function and patients with normal autonomic function. The application is operated on the server by an application service provider ("ASP"). The application determines a first discriminant equation that discriminates between the patients with abnormal autonomic function and the patients with normal autonomic function. A user may access the application with a browser over a communications network such as the Internet. The application may receive background data from a new patient and select one or more appropriate discriminant equations. The application may send the selected discriminant equations to the user's client terminal. The client terminal may then enter physiologic data from the new patient into the selected discriminant equations to produce autonomic rankings. The autonomic rankings are indicative of the new patient's autonomic function. The client terminal may then send the autonomic ranking and the physiologic data to the application. The application may use this information to determine additional discriminant equations.

Yet another embodiment of the invention entails a method of identifying certain components of physiological signals such as an R-wave of an ECG signal. The method comprises receiving a physiological signal, such as an ECG signal, from a patient and sampling the ECG signal at a predetermined sampling rate to obtain a first sample, a second sample, a third sample and a fourth sample. The samples are then filtered and the slopes between the different samples are calculated. The different slopes are then compared until a maximum slope of a waveform is located which exceeds a minimum threshold value and is less than a maximum threshold value. Cycle lengths for the detected waveform may also be compared to threshold values. Novel filtering techniques, such as using a moving average filter, are also employed.

In still another embodiment of the invention, a method for assessing autonomic function is concerned whereby a first set of ECG data is received from a patient. The first set of ECG data may have been recorded while the patient was in a substantially reclined position. The first set of ECG data is then measured to obtain a first set of HRV parameters comprised of one or more of the following HRV parameters: RMS-SD, TP, LFnorm, HFnorm, LF/HF, NN, SDNN, VLF, LF and HF. A second set of ECG data is received from the patient wherein the second set of ECG data was recorded pursuant to one or more of the following HRV tests: Orthostatic test, Metronomic test and Valsalva test. A second set of ECG data is then measured to obtain a second set of HRV parameters that are related to the Orthostatic test, Metronomic test and/or Valsalva test. Finally, the embodiment evaluates the first set of HRV parameters in conjunction with the second set of HRV parameters to evaluate the patient's autonomic function.

The foregoing has outlined rather broadly the features of the present invention in order that the detailed description of the invention that follows may be better understood. Additional features and advantages of the invention will be described hereinafter, which form the subject of the claims of the invention.

BRIEF DESCRIPTION OF THE DRAWINGS

For a more complete understanding of the present invention, and the advantages thereof, reference is now made to the following description taken in conjunction with the accompanying drawings, in which:

FIG. 1 is a flow diagram illustrating a method for measurement of autonomic nervous system function in one embodiment of the invention.

FIG. 2 is an example of a questionnaire concerning background information from a patient.

FIG. 3 is an example of a questionnaire concerning patient health information.

FIG. 4 is a block diagram illustrating a computer network for performing the processes of an embodiment of the invention.

FIG. 5 is a block diagram illustrating an exemplar data acquisition device in an embodiment of the invention.

FIGS. 6A-8 are examples of a normative database in an embodiment of the invention.

FIG. 9 is an example of a graphic display in an embodiment of the invention.

FIGS. 14A-C are examples of a normative database in an embodiment of the invention.

FIGS. 15A-B comprise a flow diagram, and accompanying table, illustrating a sequence of operations concerning ECG analysis that may be performed in accordance with an embodiment of the present invention.

FIGS. 16A-D are tables illustrating examples of HRV parameters in one embodiment of the invention.

DETAILED DESCRIPTION

1. Acquire Background Data from Patient

Figure 10:
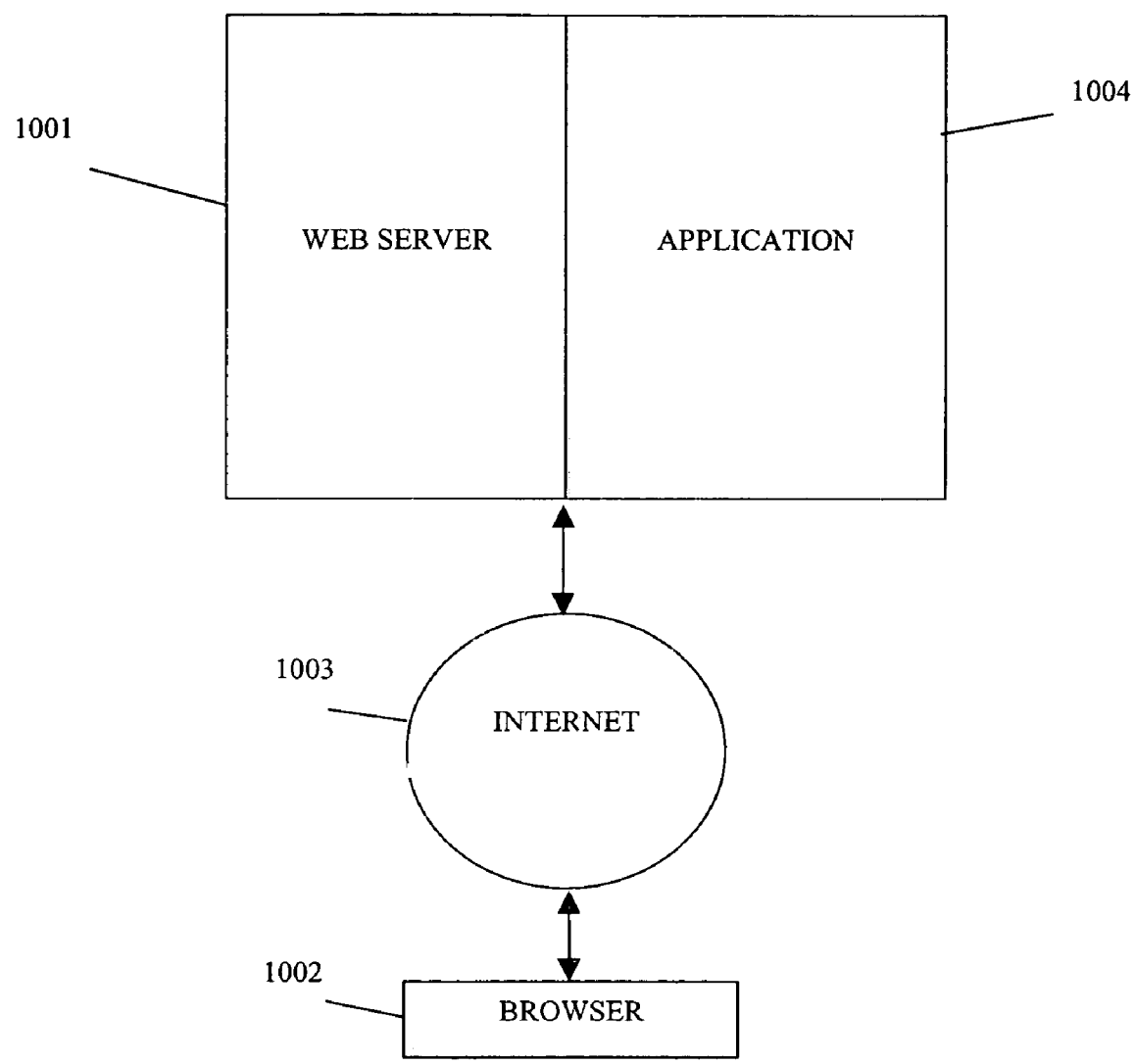
FIG. 10 is a block diagram that illustrates the modules of an embodiment of the invention.

FIG. 1 illustrates a method for measurement of autonomic nervous system function. The method begins in step 100. In step 105, background data is obtained from a patient. Such data may include, for example, age, height, weight, gender, race, smoker status and health status. FIG. 2 illustrates exemplar questions regarding the patient's background information. FIG. 3 illustrates exemplar questions regarding the patient's health history. FIGS. 2 and 3 are merely exemplar questionnaires and those of ordinary skill in the art will appreciate that more or less detailed questions or other questions can be asked. For example, the patient may be asked whether he has cancer, and if so, specifically what type of cancer. If any "medical conditions" are indicated, such as cancer, then the patient may be deemed, in a general sense, "unhealthy." If no "medical condition" is noted, the patient may be generally deemed "healthy." In addition, the clinician may make clinical observations regarding the patient and include those observations along with the data supplied by the patient. For example, the clinician may note whether the patient presents with clinical symptoms of abnormal autonomic function such as tingling sensations in the patients arms or legs. If such symptoms are present, the clinician may note the patient has abnormal autonomic function.

2. Conduct HRV tests

Returning to FIG. 1, step 110 entails autonomic testing of the patient to obtain ECG data. Such testing may occur after background information has been received from the patient in step 105. The patient may undergo provocative HRV tests such as the Metronomic Breathing test, Valsalva test and the Orthostatic test which were described in detail above. These tests are called provocative tests because a patient must provoke his nervous system, by standing up or breathing in a certain way, to produce results indicative of his HRV.

In addition to the provocative tests, a Short-Term Resting HRV test may also be used. The test is conducted over a five minute period while ECG data is recorded from a patient resting in the supine position. The patient breathes normally and in a non-provoked manner. For example, he does not time his breathing as is the case in the Metronomic test. Furthermore, he does not exhale forcefully in an effort to reach a certain air pressure as is the case in the Valsalva test. Therefore, specialized spirometric equipment is not needed. Also, patients who cannot tolerate stressful provocative measures, for health reasons, can still undergo this HRV test.

The Short-Term Resting HRV test assesses the balance between the sympathetic and parasympathetic branches of the ANS. These aspects of the nervous system have an effect on autonomic function. Historically, this test was used in limited capacities in assessing autonomic function and HRV. The limited use was due, at least in part, to the complexity associated with deriving HRV parameters from the data produced by the test. Consequently, the Metronomic, Valsalva and Orthostatic tests were favored over using the Short-Term Resting HRV test. Furthermnore, the prior art often taught that just a few parameters from the provocative tests were sufficient to assess autonomic functions.

In one embodiment of the invention, the Short-Term Resting HRV test is used in a novel way to assess autonomic function. The Short-Term Resting HRV test results are combined with results from one or more of the provocative tests to assess autonomic function. By so combining the results from Short-Term Resting HRV test and one or more provocative tests, autonomic function may be assessed in a more accurate way than is possible with the cursory prior art methods of testing autonomic function.

At least ten HRV parameters, existing in both the time and frequency domains, can be monitored in the Short-Term Resting HRV test. All of parameters are calculated on "normal-to-normal" inter-beat intervals (NN intervals), which are R-R intervals calculated on beats caused by normal heart contractions paced by sinus node depolarization. All time-domain HRV parameters are derived directly from NN intervals recorded during the test. The frequency-domain HRV parameters are derived from the power spectral density (PSD) calculated by means of a Fast Fourier Transform (FFT).

As seen in FIG. 16C, the following is a list of definitions for the time-domain HRV parameters or measurements. First, Mean NN interval ("NN") is a mean inter-beat interval value averaged over the entire ECG recording and is measured in milliseconds. Second, SDNN ("SDNN") is a standard deviation of the NN intervals that is calculated from the square root of the variance of those intervals. Variance is the mathematical equivalent to the total power of the spectral analysis. Consequently, variance reflects all cyclic components of variability in a recorded series of NN intervals. The actual values of SDNN depend on the length of recording whereby the longer the recording is, the higher the SDNN values are. Thus, one should not compare SDNN values derived from ECG recordings of different lengths. SDNN is measured in milliseconds. Third, "RMS-SD" is the root mean square of the differences in successive NN intervals. This measure is an estimate of high-frequency variations of heart rate, derived from short term NN recordings, that reflects an estimate of parasympathetic regulation of the heart. RMS-SD is measured in milliseconds.

As seen in FIG. 16D, the following is a list of definitions for the frequency-domain HRV parameters or measurements. First, Total Power ("TP") is a short-term estimate of the total power of the power spectral density in the range of frequencies between, 0 and 0.4 Hz. This measure reflects overall autonomic activity where sympathetic activity is a primary contributor. Total Power is calculated in milliseconds squared ($ms^2$) or ($ms^2$/Hz). Second, Very Low Frequency ("VLF") is a band of power spectrum range between 0.0033 and 0.04 Hz. This measure is not well defined in terms of physiologic mechanisms that cause the VLF component of the power spectrum. Generally, this parameter indicates overall activity of various slow mechanisms of sympathetic function. VLF is calculated in milliseconds squared ($ms^2$). Third, Low Frequency ("LF") is a band of the power spectrum range between 0.04 and 0.15 Hz. This measure reflects both sympathetic and parasympathetic activity. Generally, the parameter is a strong indicator of sympathetic activity in long-term recordings. Parasympathetic influence is represented by LF when the respiration rate is lower than nine breaths per minute or while taking a deep breath. Thus, when the patient is in a state of relaxation with slow and even breathing, the LF values can be very high, indicating increased parasympathetic activity rather than an increase of sympathetic regulation. LF is calculated in milliseconds squared ($ms^2$). Fourth, High Frequency ("HF") is a band of the power spectrum range between 0.15 and 0.4 Hz. This measurement reflects parasympathetic (vagal) activity. HF is also known as a "respiratory" band because it corresponds to the NN variations caused by respiration. This phenomenon is known as respiratory sinus arrhythmia (RSA). Heart rate increases during inhalation and drops during exhalation. Slow, even breathing causes an increase in the amplitude of the HF peak on the power spectrum. High Frequency is calculated in milliseconds squared ($ms^2$). Fifth, LF/HF Ratio ("LF/HF") is the ratio between the power of Low Frequency and High Frequency bands. This measure indicates overall balance between sympathetic and parasympathetic systems. Higher values reflect domination of the sympathetic system while lower ones reflect domination of the parasympathetic system. When deep and even breathing occurs, however, the elevation of this parameter reflects an increase of parasympathetic regulation due to the effect of RSA. LF/HF Ratio is calculated in normalized units. Sixth, Normalized Low Frequency ("LFnorm") is the ratio between the absolute value of the Low Frequency and the difference between Total Power and Very Low Frequency. This measure minimizes any effect of changes in Very Low Frequency power and emphasizes changes in sympathetic regulation. Normalized LF is calculated in percentile units. Seventh, Normalized High Frequency ("HFnorm") is the ratio between the absolute value of the High Frequency and the difference between Total Power and Very Low Frequency. This measure minimizes any effect of changes in Very Low Frequency power and emphasizes changes in parasympathetic regulation. Normalized HF is calculated in percentile units.

Those of ordinary skill in the art will appreciate that there are a number of alternative embodiments available which allow for patients to undergo HRV testing using other methodologies and parameters not specifically mentioned above, and that such embodiments are within the scope of the present invention.

3. Recording Equipment

FIG. 4 illustrates equipment that may be used in one embodiment of the invention. The exemplar embodiment of the invention may comprise one or more testing units 405, doctor's workstations 410 and an internet-based server 415. The testing unit 405 is used for conducting autonomic assessment tests. As illustrated in FIG. 5, the testing unit 501, may consist of a PDA 545 (personal digital assistant or handheld computer), utilizing Windows Mobile 2003 OS, or a Tablet PC, using, for example, Windows XP or Windows CE, and an ECG/Pressure acquisition device (EPAD) 550. The EPAD 550 provides, for example, functionality to measure a single-channel ECG and airflow pressure. The EPAD 550 may have three input connectors to attach standard ECG lead wires 510, in an isolated fashion, with disposable pre-gelled snap electrodes. The three ECG electrodes are typically applied approximately one inch below the middle of both collarbones and mid anterior on the medial line at ribs six and eight. The EPAD 550 may utilize individual, replaceable, 0.060 Pin connector, AHA color-coded patient lead wires. The EPAD 550 may incorporate 10 bit resolution, or more, and a frequency response of 0.05 to at least 45 Hz. The ECG signal from ECG lead wires 510 is amplified by amplifier 525 and digitized via the analog-to-digital (A/D) converter 520 using, for example, a sample rate of 300 samples/second using methods known to those of ordinary skill in the art. Hypoallergenic hydrogel electrodes combined with Ag/AgCl sensors provide reliable tracings. An exemplar electrode is the Easytrode™, available from sEMG, 202 Providence Mine Rd., Ste 202, Nevada City, Calif. 95959.

The EPAD 550 also has an input tip to connect to a spirometric mouthpiece 505, via flexible plastic tubing, for measuring airflow and pressure when breathing through the mouthpiece. The pressure signal from mouthpiece 505 is converted into electronic form via the pressure transducer 515 and is then digitized via the A/D converter 520 using methods known to those of ordinary skill in the art. The spirometric circuitry may provide for a flow range of +/−14 liters/second with a volume between 0 and 8 liters expressed in body temperature and pressure saturated with water vapor conditions (BTPS). The flow specifications may allow for the greater of +/−5% or 200 ml/sec for FEF 25%-75% (forced expiratory flow) and the greater of +/−10% or 400 ml/sec for PEF (peak expiratory flow). The same circuitry may, in one embodiment of the invention, provide volume specifications that allow for the greater of +/−3% or 50 ml for forced vital capacity (FVC) and forced expiratory volume in one second (FEV1). Elevation correction should allow for elevations of 0 to 15,000 feet. Accuracy and BTPS conditions may comply with Am. Thoracic Society Standards from 1994.

The digitized ECG and pressure signals are coupled to the processor 530. Processor 530 may execute programming instructions by which a patient's heart rate variability is analyzed in response to the measured physiological data and may take various forms, such as conventional microprocessors of a standard personal computer, workstation or other microprocessor-driven device. In one embodiment of the invention, the processor 530 is an INTEL-compatible microprocessor of IBM-compatible personal computers. The EPAD 550 may be implemented using a standard personal computer chassis with certain components (e.g., amplifier 525 and analog-to-digital (A/D) converter 520) provided in the form of circuit modules adapted for insertion into I/O ports of the computer. The memory 535 is coupled to the processor 530 and may include a Random Access Memory (RAM) for temporary data storage and/or a device with read/write access for permanent data storage, such as a hard drive. The memory 535 may be available to store physiological data until the data is transmitted to the PDA 545. This transmission may occur in numerous ways including wireless means observing the Bluetooth protocol. It will be appreciated by those of ordinary skill in the art that the techniques of the present invention may be implemented with various apparatuses, including both hardware and software. For example, the PDA 545 may receive previously recorded data from holter recordings. Doing so may allow HRV studies, such as the Short Term Resting HRV test, to be performed on previously recorded data. Consequently, ECG studies, taken for reasons completely unrelated to HRV studies, may still be analyzed for HRV purposes. The PDA 545 may also receive data from implantable devices such as pacemakers or AICD's. The devices may communicate with the PDA 545 in real time or may deliver ECG data upon interrogation by the PDA 545. Other examples of alternative HRV testing equipment include the Qmed Monitor nDx™, from Qmed Inc., and the ANScore System™, from Boston Medical Technologies, Inc.

The data may be transmitted from the EPAD 550 to the PDA 545, or directly to the doctor's workstation 410. The doctor's workstation 410, as shown in FIG. 4, utilizes software executing on, in one example, the Windows Me/2000/XP operating system. The software may be installed on any desktop or laptop computer that has, for example, USB connection capability and access to the Internet. The doctor's workstation 410 software can be programmed to automatically acquire test data from the PDA 545 every time the PDA 545 is placed on its cradle, which is connected to the PC via the USB port. The workstation 410 allows for management of test data by facilitating the following: obtaining test data from the PDA 545, viewing and verifying test data, sending test data and/or patient data to the server 415, accessing normative databases and discriminant equations for HRV assessment from the server 415, as will be discussed below, viewing and printing pre-formatted test reports, deleting test data and exporting test data to other locations. In one embodiment of the invention, the workstation 410 has at least a Pentium-II 350 MHz processor, 32 MB of RAM, video card with at least 800×600 High-Color resolution, 50 MB of free hard disk space and CD ROM drive. In other embodiments, the workstation 410 may be omitted whereby, for example, the testing unit 405 may communicate directly with the server 415. In still other embodiments, the testing unit 405 may be combined with the doctor's workstation 410 into one portable unit, such as a tablet PC. The tablet PC may communicate with the server 415.

The test evaluation server 415 may be an internet server that provides multi-user connection capability. The normative databases and discriminant functions, to be addressed more thoroughly below, may be stored on the server 415 or alternatively on the doctor's workstation 410. Many users may simultaneously connect to the server 415. The server software can provide for highly secure communication between any user and the server itself. For example, the software can have a digital certificate that encrypts data using Secure Sockets Layer (SSL) technology. The SSL security protocol provides data encryption, server authentication, message integrity, and optional client authentication for a TCP/IP connection. SSL technology is available in 128-bit encryption key strength.

Any of the four aforementioned HRV tests may be conducted using standard HRV testing equipment and methods known in the art (e.g., using the Task Force Report for Heart Rate Variability: Standards of Measurement, Physiologic Interpretation, and Clinical Use, Circulation Vol. 93. No 5, 1996, which is incorporated herein by reference).

4. Detecting R-Waves

Figure 13A:
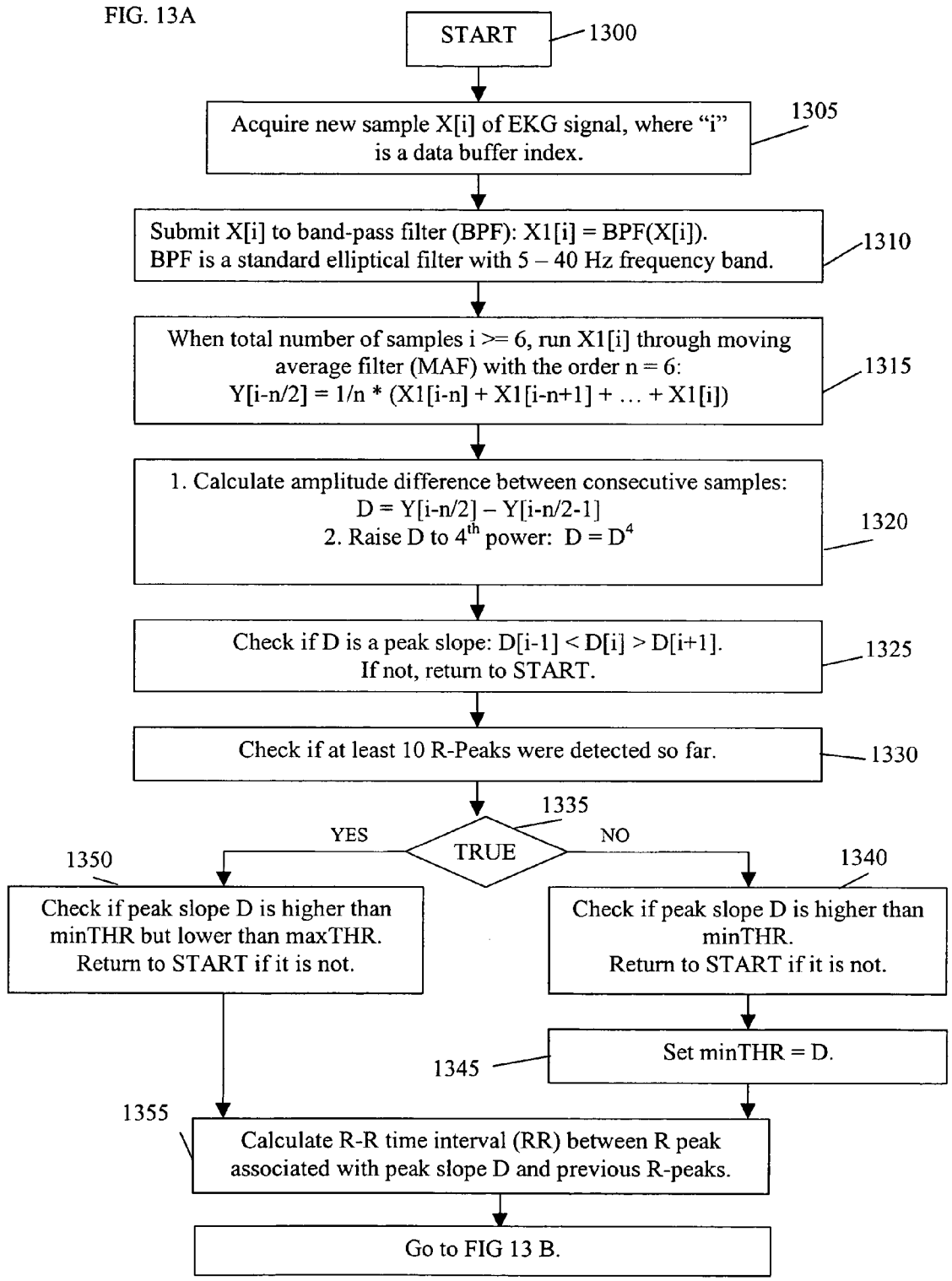
FIGS. 13A-13B are flow diagrams illustrating the sequence of operations that may be performed in accordance with an embodiment of the present invention that concerns ECG analysis.
Figure 13B:
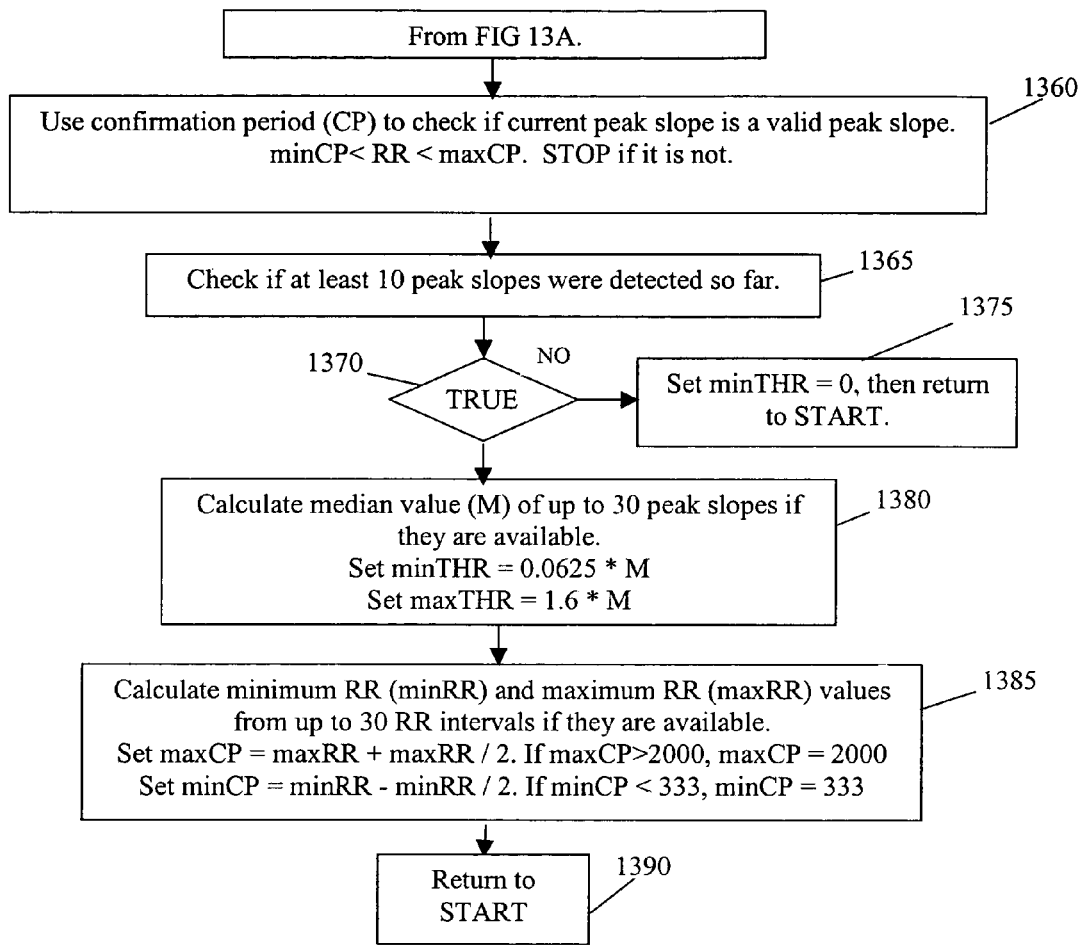

The above equipment should be able to record ECG signals because, as previously noted, HRV studies concern changes in heart rate over time. Examining the change in R-R cycle length monitors these changes. The R-R cycle length is determined by measuring the amount of time in between the R waves of two consecutive QRS complexes. FIGS. 13A-13B illustrate one embodiment of a method, which may be implemented by the above equipment, for identifying the fiduciary point of a physiological signal, such as the R-wave of an ECG signal. As those of ordinary skill in the art will appreciate, a fiduciary point is a "marker point" on, for example, a waveform whereby the fiduciary point is used to identify the location of the waveform. A fiduciary point may be the peak amplitude or peak slope on a waveform.

After beginning the process in step 1300, step 1305 commences whereby an ECG signal is received and sampled. $X[i]$ represents an exemplar sample data point. The sampling rate may be, for example, 256 samples/second, although other sampling rates may suffice. In step 1310, sample $X[i]$ is processed by a band pass filter (BPF). The band pass filter may have, for example, a pass band of 5-40 Hz, thereby removing DC, baseline drift, high frequency noise, artifact and muscle activity, which normally occupies, approximately, the 100 Hz frequency range. The band pass filter may be elliptical in nature to promote better signal quality and diminish distortion.

In step 1315, the previously filtered data is filtered once more in a moving average filter (MAF). In one embodiment of the invention, the MAF is a sixth order filter, although other orders may suffice. The MAF output is represented by the following equation:

$$Y[i-n/2]=1/n*(X1[i-n]+X1[i-n+1]+ \ldots +X1[i]).$$

Using a MAF helps ameliorate the effects of noise by examining multiple samples at once. Doing so helps diminish the effect of outlier points that may be present due to noise. In one embodiment of the invention, the MAP may average seven samples at a time, but fewer or more samples may be filtered. This moving window smoothes out the effects of noise yet avoids becoming a burden on processing bandwidth. Thus, the calculations may be done in real time The MAF plays an important role because noise is a constant problem in many HRV testing situations, especially since clinical settings may have other noise-emitting equipment in the room. In addition, the HRV equipment is often used by individuals not accustomed to proper skin preparation and electrode placement which are important for high quality ECG recordings. While the MAF is described in one embodiment of the invention, various other filtering and signal averaging techniques may be used in other embodiments of the invention. Those of ordinary skill in the art will realize the aforementioned filtering techniques may be carried out in hardware or software.

In step 1320 of FIG. 13A, the amplitude difference in consecutive samples is calculated to obtain slope. Such a calculation is represented by the following equation: $D[i]=Y[i-n/2]-Y[i-n/2-1]$, wherein $D[i]$ represents slope. To magnify the slope, $D[i]$ may be squared or raised to an exponential power, such as 4, although other powers may suffice. Choosing an even power converts negative amplitude readings into positive values, thereby accounting for negative R waves or positive R waves that read as negative R waves due to improper electrode placement. Again, electrode placement may be improper due to administration of HRV tests by individuals that lack specialized, cardiac-related experience. For example, this may occur if a patient at home uses the present invention.

In step 1325, $D[i]$ slope is compared to the preceding ($D[i-1]$) and succeeding ($D[i+1]$) slopes. If $D[i]$ is not greater than the other slopes, the process returns to start 1300 and $D[i]$ is not deemed to be an R wave. If $D[i]$ is greater than the other slopes, the process continues with $D[i]$ serving as a prospective R wave.

A peak slope is sought because R waves typically possess a frequency of approximately 20 Hz, a frequency higher than other waves found in the ECG. Therefore, finding the peak slope in an ECG complex leads to locating the R wave. The prior art typically searches for peak amplitude, instead of peak slope, in an effort to identify an R wave. Doing so may lead to high amplitude artifacts and noise being incorrectly labeled as an R wave. Because an embodiment of the present invention focuses on slope in pursuit of the 20 Hz R wave, noise with high amplitude and high frequency can be filtered out as discussed above. A maximum amplitude, which may be indicative of noise, may not be so filtered. Also, setting a maximum amplitude threshold might accidentally remove valuable R waves with high amplitudes. In addition, HRV studies are often of major benefit to older patients in predicting various maladies, and such patients often have low amplitude R waves brought on by diminished cardiac strength. The frequency of their R waves changes, however, less drastically and is therefore preferable to amplitude. In summary, the present invention's focus on maximum frequency or slope is preferable to maximum amplitude.

The peak slope, representative of what might prove to be an R wave, may next be validated to ensure it truly represents the maximum slope of an R wave. To do so requires a pool of R waves that can be compared to the prospective R wave. In step 1330, after the prospective R wave associated with $D[i]$ has been determined, the number of previously determined R waves is questioned. In step 1335, if less than a predetermined number of such R waves have been found, step 1340 is engaged. An example of such a predetermined number of R waves is ten, although other values may be used to provide a proper pool of waves. In step 1340, $D[i]$ is compared against a threshold slope value. The minimum threshold (minTHR) may be indicative of a minimum slope commonly attributed by those of ordinary skill in the art to R waves. If $D[i]$ is less than the threshold slope, $D[i]$ is determined to not be representative of a R wave and the entire ECG detection sequence begins anew at START 1300. If $D[i]$ does exceed the threshold, further validation of the prospective R wave continues. In addition, the slope threshold is set to $D[i]$, in step 1345, for future comparisons. At the beginning of the ECG detection sequence, the threshold may be set to zero.

In step 1355, an R-R interval is calculated using the prospective R wave, which is associated with a time at which $D[i]$ occurs, and the immediately preceding, previously confirmed R wave. If no previous R wave exists, the newly confirmed R wave is stored and the ECG detection process begins anew.

In step 1360, a confirmation period begins by verifying that the R-R interval, calculated in step 1355, which is associated with D[i], is greater than a minimum cycle length (minCP) and shorter than a maximum cycle length (maxCP). At the beginning of the ECG detection sequence, minCP may be set to 333 ms and maxCP may be set to 2000 ms. A typical R-R cycle length fits within these bounds. Those cycle lengths that are not within these bounds are more commonly associated with noise or other non-sinus cardiac rhythms. For example, signal artifacts, which are normally filtered out from genuine ECG data using previously described methodologies, often contain many high frequency signals, with short cycle lengths, in rapid succession. The lower bound (min CP) would help ensure these values are not labeled as R waves. The minCP and maxCP values identified above are examples only, and those of ordinary skill in the art may use other values. If the cycle length meets the requirements of step 1360, the prospective R wave is confirmed as an R wave and is no longer considered to be a prospective R wave. The R-R interval may now be used in the evaluation of many HRV parameters as previously described.

In step 1365, the number of previously determined R waves is questioned again in light of the newly determined R wave. In step 1365, if less than a predetermined number of such R waves have been found, step 1375 is engaged. An example of such a predetermined number of R waves is 10, although other values may be used to provide a proper pool of waves. In step 1375, if no such number of waves exists, the minimum threshold is set to, for example, zero. This value is set in step 1345. The ECG detection sequence then begins again in step 1300.

If there is such a predetermined amount of R waves, as illustrated in step 1380, a median value of a certain number of immediately preceding, previously detected peak slopes, each associated with a previously determined R wave, may be calculated. The selected peak slopes do not have to immediately precede the most recently confirmed R wave. There may be a maximum number of preceding R waves that may be entered into the median calculation. The maximum number is thirty in one embodiment of the invention. The median peak slope value is calculated or derived and then multiplied by a first predetermined value to obtain or derive a new minimum threshold (minTHR). The median may also be multiplied by a second predetermined value to obtain or derive a new maximum threshold (maxTHR). In one embodiment of the invention, the first predetermined value is 0.0625 and the second predetermined value is 1.6. Both values were arrived at empirically and are only exemplar values. Other values may be used. In addition, mean, average or mode values, or similar methods related thereto, may be substituted for median values.

In step 1385, the minCP and maxCP are reevaluated in light of the newly confirmed R wave. These values may be obtained by finding the minimum R-R cycle length (minRR) and maximum R-R cycle length (maxRR) from a certain number of immediately preceding, previously detected peak slopes, each associated with a previously determined R wave. The selected peak slopes do not have to immediately precede the most recently confirmed R wave. There may be maximum number of preceding R waves that may be analyzed. The maximum number is thirty in one embodiment of the invention. Once minRR and maxRR have been found, maxCP and minCP are derived or calculated as follows:

$$maxCP = maxRR + maxRR/2$$

$$minCP = minRR - minRR/2$$

These formulae simply set CP thresholds equal to maximum and minimum R-R intervals, found within a set of R waves, with 50% tolerance. The level of tolerance is an empirical value and may be adjusted in other embodiments of the invention. For example, a 0% tolerance may equate maxCP directly to maxRR. If maxCP>2000, the newly calculated maxCP is reset to 2000. If minCP<333, the newly calculated minCP is reset to 333. These values, as previously described, are known to those of ordinary skill in the art as reasonable bounds for R-R intervals. In step 1390, the ECG detection process ends or loops back to step 1300.

In subsequent iterations of the ECG detection scheme, the predetermined number of previously determined R waves, as set out in step 1330, will eventually be met. Then, step 1350 may be performed. A newly determined slope may then be compared to the new minimum and maximum thresholds determined in step 1380. These values help to verify if a prospective R wave bears a resemblance to the median value of previously determined R waves. If the prospective R wave is random noise or an artifact, it would likely not pass this test. In addition, waves with smaller slopes, such as the P wave, would not exceed the minimum threshold. Because the median values may be calculated on the thirty most recently determined R waves, for example, the threshold values are adaptive to true changes in heart rate which may have been brought on by any number of factors, including provocative measures undertaken in HRV testing. After step 1350, confirmation of the prospective R wave continues as previously described and as indicated in FIG. 13A. One of ordinary skill in the art will appreciate that there are a number of alternative embodiments available which allow for R wave detection and that such embodiments are within the scope of the present invention.

The ECG detection sequence, in its many embodiments, has several advantages over the prior art. The sequence helps combat noise and thereby identifies R waves more accurately. The method also provides flexibility in contrast to the rigid systems represented by the prior art. Such flexibility exists in, for example, the method's ability to adjust boundaries (e.g., minTHR) according to patient data that is received by the system. In addition, the resultant ability to accurately measure R-R cycle lengths, in real time, helps a clinician terminate a lengthy study, such as the 5 Minute Resting HRV study, if poor signals are being generated. Then, for example, electrode patches can be re-applied and the test can begin again. Those of ordinary skill in the art will appreciate that the invention is not limited solely to ECG data. Various embodiments of the invention may be used to detect, for example, EEG, EMG, blood pressure and other physiological signals that comprise waveforms with slopes and/or cycle lengths. The analysis of varied physiological signals is within the scope of the invention.

5. Further Verifying R Waves

Figure 15A:
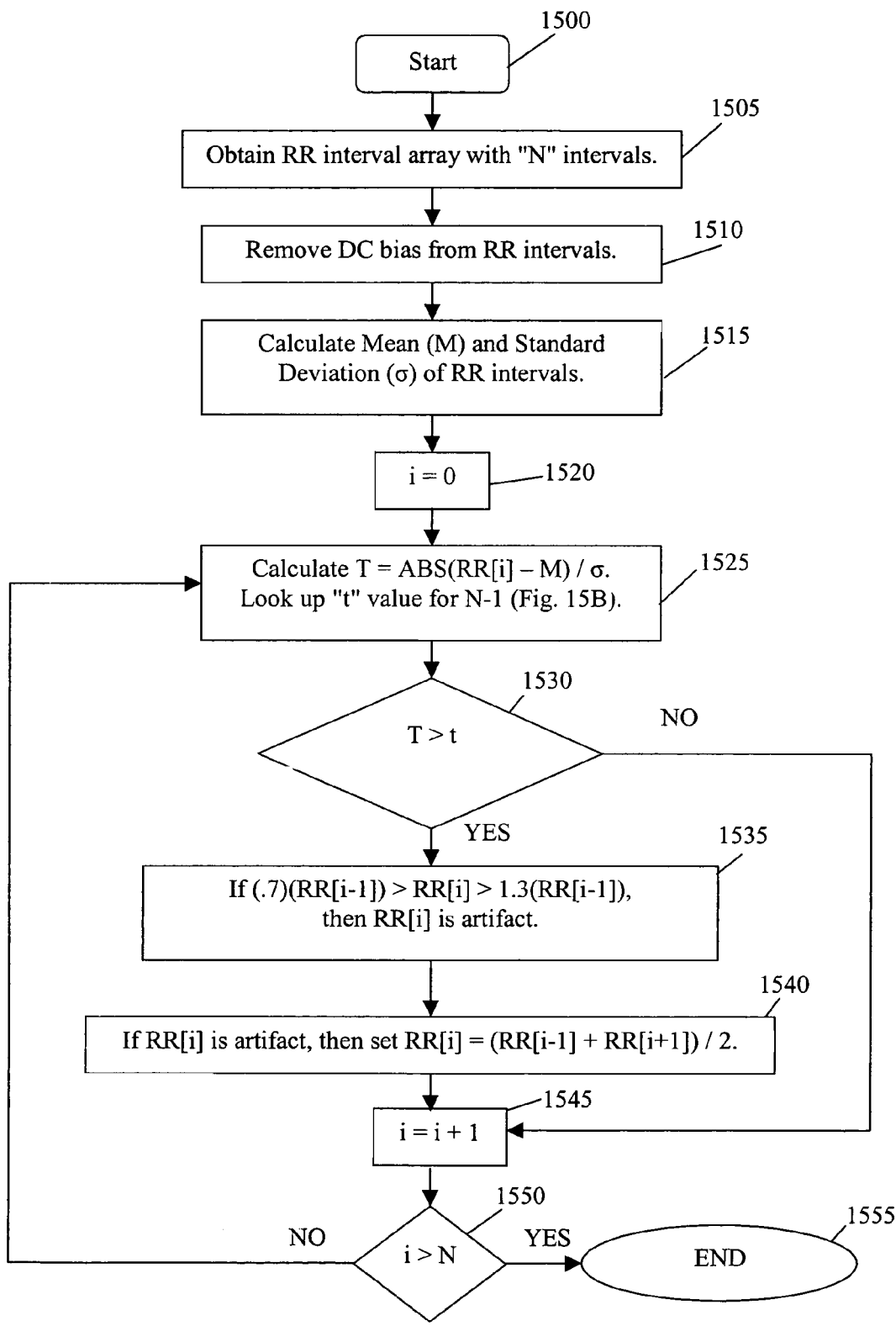

FIG. 15A illustrates an embodiment of a method for further verifying that the above process has accurately detected R waves. The method helps distinguish abnormal waves from normal R waves. The abnormal waves may be, for example, artifact signals produced by sources other than the heart. Such artifact may be due to a clinician contacting a loose electrode. Other examples of abnormal waves are ectopic heart beats that produce R waves. These R waves represent heart activity other than normal waves originating from sinus node activity.

An embodiment of the verification method begins at 1500. In 1505, a sample array of "N" RR intervals is collected. DC bias is removed from the intervals in 1510.

The mean ("M") and standard deviation ("σ") of the intervals is calculated in 1515. In 1520, the interval ("i") to be examined is set to "0". Using statistical methods known to those of ordinary skill in the art, in 1525 a "T" value is calculated as follows: T=absolute value of (RR[i]−M)/σ. In addition, a "t" value is ascertained using FIG. 15B. A t value is a statistical value related to the degrees of freedom for a data set. For example, for an array of 15 RR intervals, the "N-1" degree of freedom value is 14 and the corresponding t value is 2.24. In 1530, T is compared to t. If T is not larger than t, RR[i] is likely not an abnormal beat. Consequently, in 1545 the next interval, RR[i+1], inset to be examined. If 1550 indicates RR[i] was not the last interval in the array, the process begins anew as 1555 returns to 1525 to begin analysis of RR[i+1]. If RR[i] is the last interval in the array, 1555 returns the process to 1500 to begin analysis of a new array of RR intervals.

In 1530, if T is larger than t, RR[i] may be an abnormal beat and must be analyzed further. In 1535, if RR[i] is less than 70% of RR[i−1] or more than 130% of RR[i−1], RR[i] is deemed an abnormal beat which may be indicative of artifact or, for examnple, an ectopic beat. In 1540, RR[i] may be set to a point that is interpolated between preceding and proceeding valid RR intervals. The interpolated point may be defined as follows: RR[i]=(RR[i−1]+RR[i+1])/2. Consequently, the abnormal wave, in its original form, is removed from further analysis. More specifically, time domain analysis of the array will not consider those RR intervals preceding and proceeding the abnormal signal. However, in frequency domain analysis, the artifact is adjusted so that the R wave is still analyzed but only at its interpolated position and not its original position. In 1545, the next interval, RR[i+1], is set to be examined. One result from this verification process is that abnormal waves that were previously identified as R waves are no longer so identified. The method is known to those of ordinary skill in the art and is further described in the following article: D. Sepetliev, *Statistical methods in medical scientific research* (Medicine, Moscow, 1968), which is hereby incorporated within.

The clinician may still wish to further verify that the R waves were accurately detected. In one embodiment of the invention, the clinician may view a display that illustrates a 5 second window of ECG data. Within the window, each normal and abnormal R wave is identified with, for example, a marker that may be in the form of a cross-hair. FIGS. 13A-13B addresses detection of normal R waves. So that the clinician has a general idea of where the 5 second window is taken from, a graph that tracks HR throughout the ECG recording is displayed. The section of the HR graph that pertains to the selected 5 second ECG window is highlighted. If the clinician locates a normal R wave not identified by the invention, he may mark the missed wave, through use of a graphical user interface (GUI), so that the system will now recognize the missed wave as a normal R wave. If there are waves, such as artifacts, that have been incorrectly identified by the invention as an R wave, the clinician may remove the marker using the GUI. If an ectopic beat has been marked as a normal R wave, the clinician may use the GUI to toggle the identification to one representing an abnormal R wave. The clinician may repeat this process, by moving from one-5 second window to another 5-second window, until the entire ECG recording has been analyzed.

6. Generate HRV Parameters

Again referring to FIG. 1, once the autonomic tests have been administered in step 110, the resultant ECG data is measured and HRV parameters may be obtained in step 115. The exact HRV parameters generated are a function of which autonomic tests are administered. For example, the HRV parameters measured in the Metronomic test may include one or more of the following parameters listed in FIG. 16B. The HRV parameters measured in the Orthostatic test may include one or more of the parameters listed in FIG. 16A. The Valsalva ratio is measured during the Valsalva test. Finally, for the Short-Term Resting HRV test, one of more of the HRV parameters listed in FIGS. 16C-D may be derived. While the Metronomic Breathing test, Valsalva test, Orthostatic test and Short-Term Resting HRV test may result in the twenty-two exemplar parameters just listed, other HRV parameters exist and may be used.

7. Determine Whether Normnative Database Exists

Initially, no database of test results may exist from which normative values may be derived. Consequently, in step 110, a statistically significant number or population of individuals must be tested in order to generate data that can be gathered and compiled into a database. Such a population may be tested according to any number of HRV tests including the Slow Metronomic Breathing test, Valsalva test, Orthostatic test or Short-Term Resting HRV test. Assuming, in step 120, that no such database exists initially, step 125 calls for the addition of the patient data obtained in steps 105 and 110 to be added to the database, which may reside on the server 415. Patient data should continue to be collected at least until a statistically significant data set from a population of patients is achieved. What may constitute such a statistically significant data set will be discussed in more detail in conjunction with step 135.

8. Perform Discriminant Analysis

As test results and patient information are entered into the database, discriminant analysis of the data may begin in step 130. The data set can be classified according to any number of variables such as, for example, type of test administered (e.g., Metronomic and/or Orthostatic), parameters monitored (e.g., E/I ratio and/or SDNN), age, gender, race, smoking history and health condition (e.g., whether a patient has pancreatic cancer or simply whether a patient is healthy or ill). Healthy individuals may be included in addition to those with conditions such as diabetes or heart disease. Subsets of these variables may indicate the severity of AN related to maladies such as diabetes. On a more general note, the patients in the data set may be given a preliminary classification that helps measure the severity of various health conditions. For example, each patient in the data set may have a health classification such as "no autonomic dysfunction", "borderline dysfunction" or "clinically evident autonomic dysfunction."

In the following example of a data set, a group of 128 patients took the 5-min resting HRV test, Slow Metronomic Breathing test and Orthostatic test. All patients were 30-35 year old white, non-smoking men. The group consisted of two subgroups: 64 "healthy" patients and 64 patients with clinically evident diabetic autonomic dysfunction. The data set, comprised of background data and HRV parameters from the population of patients, was then subjected to statistical discriminatory analysis. Statistical discriminatory analysis is used to determine one or more discriminant equations wherein each such equation discriminates between, for example, patients with abnormal autonomic function and patients with normal autonomic function. Doing so indicates whether a pattern indicative of autonomic dysfunction could be found for similarly situated individuals.

Discriminant function analysis is a statistical tool used to determine which variables discriminate between two or more naturally occurring groups. For example, the analysis can be used to investigate which patient information and autonomic test parameters discriminate between individuals with autonomic dysfunction, individuals without autonomic dysfunction and borderline individuals that lie between these classifications. Discriminant analysis can then be used to determine which variable(s) are the best predictors of autonomic dysfunction. In a stepwise discriminant function analysis, such as the one used in the present example, a model of discrimination is built step-by-step. Specifically, at each step, variables are reviewed and evaluated to determine which one will contribute most to the discrimination between groups of patients. If such a contribution is made, that variable will then be included in the later analysis and the process starts again until all variables have been examined. The statistical methods incorporated in this example are known to those of ordinary skill in the art. In addition, the particular statistical analysis employed in the invention need not be the exact analysis described herein. Those of ordinary skill in the art will readily realize that other statistical methodologies may be employed to identify patterns within the data set.

Keeping with the present example, twenty-one HRV parameters, derived from three HRV tests, were gathered for all 128 patients. This data is provided in FIGS. 6A-I. These test results were processed with a standard forward stepwise linear discriminant analysis. The Statistica™ 5.0 software package was used to provide this analysis, with the following parameters set for the method: Tolerance=0.010, F to enter=1.00, F to remove=0.00 and Number of steps=21 (i.e., the number of parameters to be analyzed). F is essentially computed as the ratio of the between-groups variance in the data over the pooled (average) within-group variance. If the between-group variance is significantly larger, then there must be significant differences between means. The stepwise procedure is guided by the respective "F to enter" and "F to remove" values. The F value for a variable indicates its statistical significance in the discrimination between groups. In other words, it is a measure of the extent to which a variable makes a unique contribution to the prediction of group membership. Statistica™ software is available from StatSoft, Inc., 2300 East 14th Street, Tulsa, Okla. 74104. The above-identified values are provided as examples only and may be modified by those of ordinary skill in the art in accordance with their statistical analysis design choices.

The discriminant analysis derived (i) a discriminant equation that (ii) determined 8 of the 21 parameters were statistically significant. The data for these 8 parameters, a subset of data presented in FIGS. 6A-I, is presented in FIGS. 14A-C. A focus on 8 of the 21 parameters demonstrated a pattern that significantly separated patients with autonomic dysfunction from those without autonomic dysfunction. The discriminant analysis indicated the other 13 parameters were not statistically relevant in discriminating between patients afflicted with autonomic neuropathy due to diabetes and those patients with normal autonomic function. The significant parameters for the 5-min Resting HRV test were RMS-SD and TP. The significant parameters for the Slow Metronomic Breathing test were E/I Ratio, SD and NNmin SB. Finally, the significant parameters for the Orthostatic test were 30:15 Ratio, NNmin Standing and NNmax Standing. A description of these parameters was set out above.

The newly derived discriminant equation is as follows:

$$Y = (21.7134 * E/I \text{ Ratio}) + (0.0936 * SD) - (0.0628 * RMS\text{-}SD) + (0.0008 * TP) + (3.7881 * 30:15 \text{ Ratio}) - (0.0020 * NN\text{min } SB) - (0.0100 * NN\text{min Standing}) + (0.0056 * NN\text{max Standing}) - 39.6343.$$

Essentially, this equation was derived so that, when the 8 relevant factors are input into the equation, any resultant Y value that is positive will be indicative of a patient with normal autonomic function. Any resultant Y value that is negative will be indicative of a patient with autonomic neuropathy due to diabetes. Those variables with the largest coefficients are the ones that contribute most to the prediction of autonomic dysfunction. Thus, in this example, the E/I ratio contributes most to the prediction because its coefficient is larger than the other coefficients.

While one discriminant equation has been identified in this example, an embodiment of the invention concerns finding one or more such equations. For example, a second equation could be derived from the same data representative of the 21 HRV parameters recorded for the above example. The first discriminant equation discriminated between patients of a population that had a first autonomic state, such as diabetes and autonomic neuropathy, and other patients in the same population that had a second autonomic state, such as no autonomic neuropathy. A second discriminant equation might distinguish between patients with a first autonomic state, such as hypertension and autonomic neuropathy, and other patients with a second autonomic state, such as normal autonomic function and no hypertension.

Those additional equations may continue to be derived as the normative databases receive more background information and test results. Using the new data, the invention could determine an equation for discriminating between those with both coronary artery disease (CAD) and diabetes and those that have neither condition. In addition, the invention could determine another equation for discriminating between those individuals with CAD, and associated autonomic dysfunction, and those without autonomic dysfunction. Also, the invention could determine an equation for discriminating between individuals with CAD, who would have a first state of autonomic function indicative of CAD, and those with diabetes, who would have second state of autonomic function indicative of diabetes. The multiple equations, possibly derived from multiple HRV parameters taken from multiple HRV tests, provide for more accurate autonomic assessment of patients than was ever possible with prior art methods that failed to consider such discriminant equations. In short, the multiple equations allow for like individuals, such as white, 30-year old males, to have their HRV test results compared against other white, 30-year old males. Multiple equations may allow that same white, 30-year old male to have his results, using one equation, compared against 30-year old, white males with hypertension and, using a second equation, against 30-year old, white males with diabetes. In doing so, the patient's autonomic function is assessed in a more accurate and precise manner than would be the case with prior art methodologies.

Returning to the example with 128 patients, after a discriminant equation was derived, the 128 patients' test data were entered into the equation to calculate the outcome, or root, of the discriminant function. The outcome values are presented in FIG. 7A-7D. These outcomes may be identified as an autonomic ranking or autonomic dysfunction rank (ADR).

In one embodiment of the invention, when the ADR is greater than 0, the patient is considered healthy. When ADR is equal to, for example, 0, the patient is still healthy but could be considered "borderline" for autonomic dysfunction. As an ADR grows negative, a more severe autonomic dysfunction is indicated. Autonomic pathophysiology indicates there is a gradual transition, through a "borderline" phase, from a healthy condition to a pathological one.

Taking this approach, a "borderline zone" may be defined, for example, as plus/minus 5% of the variance of the discriminant function derived from the entire set of 128 patients. Therefore, if ADRmin=−12.1825 and ADRmax=11.3844, then R=23.5669 and the borderline zone will range from −1.1784 to +1.1784.

9. Store Discriminant Equation

The newly derived equation should be added to a database, step 135, along with any previously derived and still valid equations, for use with future patients. In one embodiment of the invention, the process is continued until a statistically significant number of patients have been examined and one or more discriminant equations have been derived. As an example of achieving a statistically significant data set, analyzing patterns among patient gender, fourteen different categories of age, five categories of race, and two categories of health (e.g., those with and without clinically evident autonomic dysfunction) may require 12,500 patients assuming each unique combination of variables should have about 44 data points recorded.

12,500 patients were pursued in the present example for at least the following reasons. In discriminant analysis, the number of observations for a group that will be studied should be higher than the total number of parameters that will be tested for that group. Therefore, using all four previously described HRV tests will produce 22 HRV parameters. Consequently, more than 22 observations should be made for each group that will be studied. To be conservative, 44 data points were gathered, which doubles the required minimum number of observations (22). Regarding the number of groups to be studied, two patient genders, fourteen different categories of age, five categories of race, and two categories of health result in 280 different groups or types of patients that were to be studied. 280 groups multiplied by 44 data points per group equates to 12,500 tests that should be considered. While a specific example of what constitutes a statistically relevant population has been addressed herein, a determination of when a statistically valid amount of data has been collected is well known to those of ordinary skill in the art and may vary from that described above.

10. Choose Applicable Discriminant Equation for New Patient

Moving back to step 120 in FIG. 1, once a normative data set has been created from a statistically significant population of patients, new patients may be evaluated in relation to the norms found within the population data set. In one embodiment of the invention, the new patient is subjected to the Metronomic Breathing test, Valsalva test, Orthostatic test and Short-Term Resting HRV to produce ECG data in step 110, after first having background data taken in step 105. The ECG data is then measured to obtain HRV parameters in step 115. One may choose to use multiple tests because an autonomic abnormality may manifest itself in, for example, the Valsalva test but not the Orthostatic test. Patients with specific severe cardiac conditions, however, may only be capable of Short-Term Resting HRV testing due to the patient's elevated risk for abnormal cardiac events.

In step 145, a new patient that is, for example, a 35 year old, white, non-smoking man with clinically evident signs of autonomic dysfunction caused by diabetes (Patient 1) is evaluated against the discriminant equation derived earlier. In addition, a 31 year old, white, non-smoking man who is apparently healthy (Patient 2) is also evaluated against the above discriminant equation. However, the above discriminant equation may not be selected for a 30 year old, Hispanic, smoking woman with clinically evident signs of autonomic dysfunction caused by CAD because the above equation is based on data from 30-35 year old white, non-smoking men. Still, an investigator may choose to evaluate the exemplar Hispanic woman against all known discriminant equations, including the one that is the subject of the present example, associated with individuals aged 30 to 35 years. In contrast, the investigator may choose to compare the exemplar Hispanic woman only with other smoking, 30-year old Hispanic women. Therefore, in one embodiment of the invention, one or more discriminant equations are selected in response to the background data from the new patient. This selection may be preformed automatically by the invention or manually by the clinician.

11. Generate Autonomic Ranking

Using Patients 1 and 2 as examples, the patients may be subjected to, for example, the 5-min resting HRV test, Slow Metronomic breathing test and Orthostatic test, producing HRV data as shown in FIG. 8. These results should contain all eight parameters values called for by the previously derived exemplar discriminant equation. In step 150, the eight HRV parameters are input into the selected discriminant equation to produce autonomic rankings, as seen in step 155, that are indicative of the patient's autonomic function, as follows:

Patient 1:
$$(21.7134*1.1075)+(0.0936*31.48)-(0.0628*27.51)+\\(0.0008*63.64)+(3.7881*1.083)-(0.0020*572)-\\(0.010*372)+(0.0056*592)-39.6343=-11.828\\(ADR)$$

Patient 2:
$$(21.7134*1.3966)+(0.0936*110.76)-(0.0628*52.63)+\\(0.0008*1020.37)+(3.7881*1.349)(-0.0020*748)-\\(0.0100*620)+(0.0056*936)-39.6343=1.1659\\(ADR)$$

12. Present Autonomic Rankings to Clinician

Although the discriminant function produces a positive autonomic ranking of 1.1659 for Patient 2, the value falls into the borderline zone, instead of normal or abnormal zones, as illustrated in step 160 and by Point 910 in FIG. 9. Even though there is no clinical manifestation of autonomic dysfunction, the patient will be considered "borderline." Thus, while Patient 2 showed no clinically evident signs of autonomic dysfunction, he is clearly at risk for developing such dysfunction. The autonomic ranking may be classified as being indicative of a propensity for Patient 2 to develop a specific illness such as diabetes. Considering many individuals have autonomic dysfunction that does not manifest itself clinically, the results for Patient 2 are critical. Patient 2 can now work with his clinician to manage his lifestyle towards autonomic improvement. Furthermore, the effects of any prescribed regimen can be evaluated when subsequent test results are compared to the first autonomic ranking. Concerning the exact display illustrated in FIG. 9, one of ordinary skill in the art will appreciate that the autonomic ranking may be presented to the clinician or patient in many different ways and that the various display embodiments are within the scope of the present invention. For example, an exemplar display may be three dimensional with clouds or sectors that identify different scores that are indicative of different maladies. The patient's ADR could then be plotted in view of these clouds or sectors. The patient may then readily realize his proximity to different maladies. The clinician may then order specific tests for maladies that the patient is at risk for contracting. The clinician may also make referrals to, for example, an oncologist for a patient who is borderline for pancreatic cancer. In one embodiment of the invention, the referral to other doctors or necessity for other tests may be performed automatically by the invention.

Returning the above example, in contrast to Patient 2, Patient 1 has a very negative autonomic ranking of 11.828. This ranking confirms the clinical assessment of autonomic dysfunction. Now that Patient 1 has an objective ranking to corroborate his clinical assessment, he may more easily monitor the effectiveness of therapy or a change a lifestyle upon his autonomic function by comparing his future autonomic rakings with the present ranking. Along these same lines, pharmaceutical companies may easily track the efficacy of certain drugs by using these HRV results.

13. Amend Normative Database

After step 155 and, for example, step 160, some or all of Patient 2's background information, HRV data and ECG data may be added to the normative database where discriminant analysis may again be performed. This step allows for the database to consider additional data that is of critical import for HRV analysis, especially considering the possible lack of normative values addressing, for example, the relationship between HRV and CAD or the relationship between race, smoking status, pancreatic cancer and HRV.

In one embodiment of the invention, a patient's autonomic ranking for condition 1, obtained in year 1, may later be compared with the patient's autonomic ranking for condition 1, obtained in year 2. The normative values may be archived on the test evaluation server 415 as the normative database grows to ensure a patient's autonomic test results in year 2 can be compared against normative values from year 1. Similarly, a patient's test results from year 1 can be archived so they can later be compared with normative values from year 2, thereby allowing a health care provider to more fully take advantage of updated normative values as they develop. In this way, the invention could periodically test prior test results against updated normative values to determine if a patient's autonomic ranking should be revised in light of improved normative values and/or newly derived discriminant equations.

Thus, an alternative embodiment of the invention entails ongoing health care for the patient. As HRV testing becomes more popular with clinicians, normative databases will be more populated with data. As these normative databases grow, new discriminant equations will be derived or determined and previously determined discriminant equations may be modified.

Returning to the above example concerning Patient 1, a clinician may continue to monitor Patient 1 over time. For example, the clinician may input Patient 1's HRV test parameters from Patient 1's initial HRV test into a newly determined discriminant function, derived from background data and physiologic data from a second population of patients, to produce an alternative, or new, autonomic ranking. The alternative ranking may indicate that Patient 1's initial HRV parameters, which produced a "borderline" ranking, may now indicate an "abnormal" ranking based on updated normative values. The invention could then alert the clinician to contact Patient 1 to reassess any prescribed therapy or to conduct further testing, such as a test for diabetes in Patient 1's case. In one embodiment of the invention, the patient's various autonomic rankings are displayed in proximity to one another so the patient can readily appreciate how his autonomic function has changed over time.

In yet another alternative embodiment, the clinician may collect new physiologic data, such as ECG readings and the resultant HRV parameters, from Patient 1. The clinician may then input the additional physiologic data from Patient 1 into the initially derived discriminant function to produce a second autonomic ranking, wherein the second autonomic ranking is indicative of Patient 1's alternative autonomic function. The two autonomic rankings could then be compared with one another to determine how Patient 1's autonomic function is progressing. The embodiment of the invention could indicate to the clinician that there has been a change between the two autonomic rankings that exceeds a predetermined amount. If the change was for the worse, the clinician could then order needed tests, such as a test for diabetes in Patient 1's case. As an additional embodiment, Patient 1's new physiologic data could be input into newly derived discriminant equations to provide up to date autonomic function results. The two autonomic rankings could be displayed in proximity to one another thus facilitating comparisons between the two rankings.

As a normative database grows, the discriminant equations will become more discriminating and be able to connect autonomic rankings to indicators of whether a patient suffers from, or is at a heightened risk for contracting, a specified illness, such as for example, diabetes, coronary artery disease, anxiety, depression, sudden cardiac death, myocardial infarction and hypertension. Other HRV-related maladies are described further in the Task Force Report for Heart Rate Variability: Standards of Measurement, Physiologic Interpretation, and Clinical Use, Circulation Vol. 93. No 5, 1996, which is incorporated herein by reference. Those of ordinary skill in the art will readily appreciate that the methods and apparatuses described herein may be used to identify other maladies not specifically mentioned or described and that identification of such maladies is included within the scope of the invention.

The end result of steps 100 through 160 is that a patient with certain characteristics can be compared with like individuals in a very specific and accurate fashion. Thus, the normative database, discriminatory equations, autonomic test parameters and background patient data will allow a forty year old, white man with pancreatic cancer and a history of heavy smoking to have his autonomic data compared with like individuals to determine his predisposition for maladies found within those like individuals.

One of ordinary skill in the art will appreciate that there are a number of other alternative embodiments available which allow for the identification of autonomic dysfunction patterns and for the application of the identified patterns to new patient data, and that such embodiments are within the scope of the present invention. In addition, the various embodiments of the invention are not directed solely towards traditional HRV testing. For example, certain embodiments of the invention may be used for HRV and spirometric testing of non-human animals, such as horses, cattle, dogs and cats, are within the scope of the invention. The invention may be used in other non-traditional settings. For example, embodiments of the invention may be used for battlefield or civilian assessment of biological warfare efforts. HRV testing may evaluate whether an individual has been exposed to a toxin or a chemical or biological agent. The effects of such agents may have immediate or delayed expression in the afflicted individual. This expression may manifest itself by a decrease in autonomic function. The various embodiments of the invention may be used to detect such a decrease in autonomic function. Embodiments of the invention may then monitor improvements in the autonomic function as well. In short, one of ordinary skill in the art win appreciate that application of the invention is not limited to traditional HRV testing and that non-traditional uses of the invention are encompassed with in the scope of the invention.

14. Application Service Provider Model and Other Alternative Embodiments

An alternative embodiment of the invention concerns an Application Service Provider ("ASP") model. Generally, in an ASP model, a business offers software application capabilities, from centralized data centers via wide area networks, including the Internet, to remote users. For users, an ASP is a kind of outsourcer wherein users are not required to buy and own software applications accessed from the ASP. For example, Microsoft may provide to users access to the most current versions of applications such as Microsoft Word and Microsoft Excel over the Internet from a web server running such applications. Microsoft may then charge the users on a per use basis. Generally, in the long run such programs will be more up to date than the off the shelf versions available for purchase by users. Another advantage of the ASP model is that users can run available applications with a thin client, also known as NetPCs or NetStations. The ASP will provide such thin clients with access to applications such as word processing and spreadsheet applications, will store a user's personal files, and provide all necessary processing power for running such applications.

Referring to FIG. 10, there is illustrated a block diagram of an ASP system configured in accordance with an embodiment of the present invention. A user at their client machine with a browser 1002 loaded thereon has access to the Internet 1003. Please note that the present invention should not be limited to the Internet, but is also applicable to any local area network, wide area network, or global communications network. The user will type in a URL into their browser 1002 to access the web server 1001 of the ASP they desire to contact. Once the user has accessed the ASP, the user will then be able to select an application 1004 being run on the ASP's web server 1001. Such an application 1004 could be a spreadsheet program, such as Microsoft Excel or an application for measuring autonomic function. In such a process, instead of the user having to purchase the software for the application and load it onto their client machine, the user may use their browser 1002 to access all of the features of the application 1004 over the Internet 1003 through the web server 1001 of the ASP. Typically, GUIs (graphical user interface) of the application will be sent to the user for viewing on their browser 1002, and the user will insert data, for example a letter or memo they wish to create in a word processing application, which data will be uploaded from the browser 1002 to the application 1004 running on the web server 1001 of the ASP. The process for performing this function is well known in the art.

Figure 11:
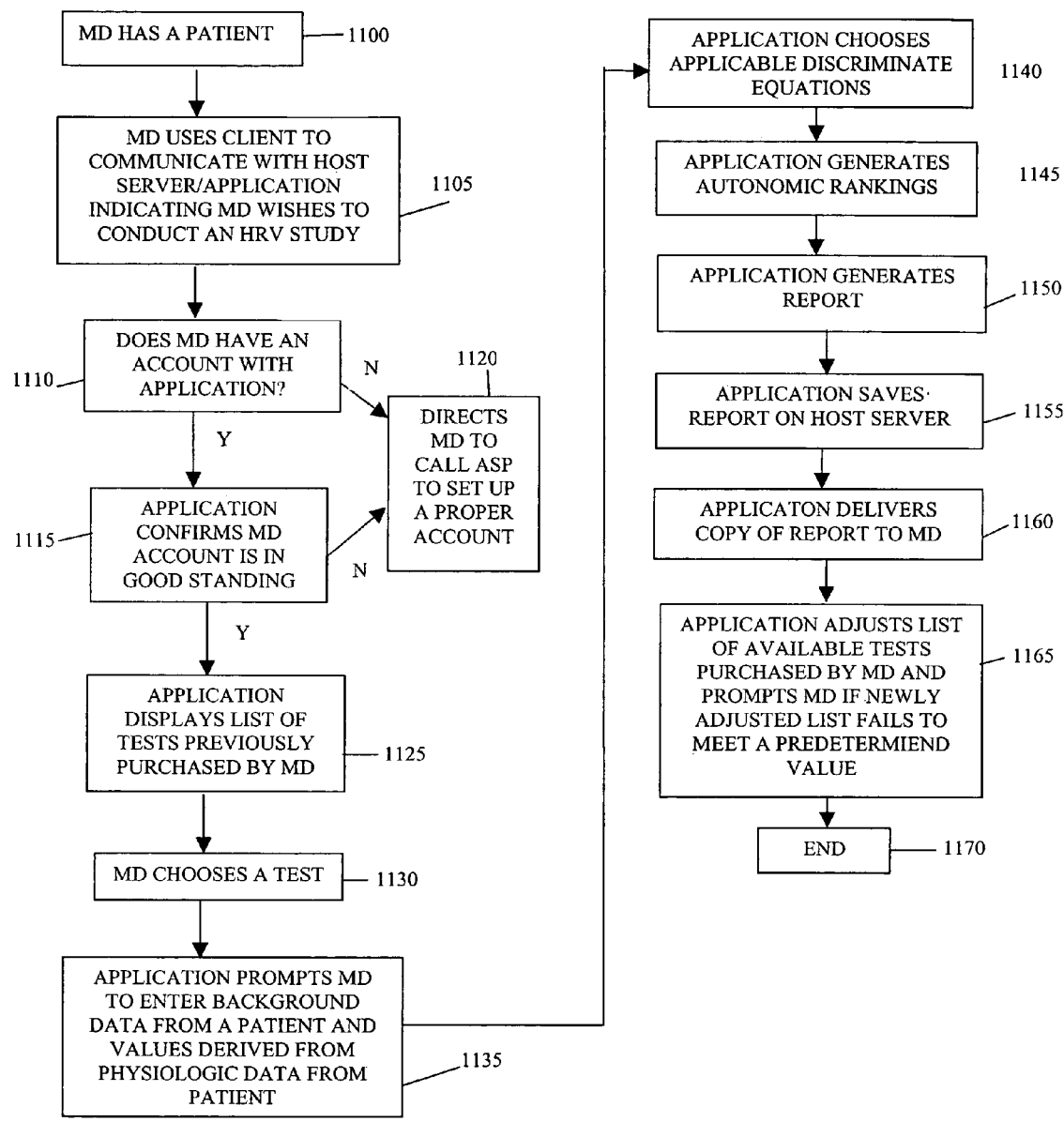
FIG. 11 is a flow diagram illustrating the sequence of operations that may be performed in accordance with an embodiment of the present invention that uses an ASP model.

For example, in FIG. 11, once a clinician (MD) has a candidate (patient) (step 1100) for HRV testing, in step 1105, he may use a browser 1002, located on his workstation 410 or testing unit 405, to access the web server 1001 (i.e., test evaluation server 415) and application 1004. In step 1110, if the clinician has an account with the ASP, he may log in to the application 1004. In step 1120, if no such account exists, he may contact the ASP to open an account. Once the application 1004 confirms the clinician has a viable account in step 1115, the application 1004 may display a list of available tests in step 1125. These tests may be packaged in any number of ways. The display may, using a pull down menu, as an example, offer the clinician the option of selecting one Valsalva test and one Metronomic test. The display may offer, however, tests in packages, where purchasing one test package amounts to purchasing one Metronomic test, one Valsalva test, one resting HRV test and one Orthostatic test.

Each test may have a unique identifier assigned to it. This unique identifier may be used for billing purposes by the application 1004. For example, the unique identifier may be associated with receivables such as spirometric mouthpieces. When the clinician purchases a Metronomic test, the ASP may also bill the clinician for the mouthpiece that is required for use with the test. The mouthpieces may have been shipped, in bulk, to the clinician at an earlier time. This may further aid in other billing concepts. For example, a clinician could be billed for 10 spirometric mouthpieces after 10 HRV tests have been purchased. A unique identifier may also be assigned to the patient. This will facilitate tracking the patient's medical records because the identifier would be stored or coupled to the server 1001. For example, while a patient may discontinue seeing a particular clinician, the patient would not have to transfer his files to the office of another clinician. The second clinician could access the patient's medical files using the patient's unique identifier, a browser 1002, the internet 1003, the application 1004 and the server 1001. The unique identifier of the patient may be linked to the unique identifier associated with the test. The patient information could be protected in any number of ways, including using the Secure Sockets Layer (SSL) technology SSL described earlier.

In step 1130 of FIG. 11, the clinician chooses a test. The application 1004, in step 1135, then may prompt, using a dialog box for example, the user to enter background data from a patient as well as physiologic data from a patient into the application. This step may be implemented in an automatic fashion whereby, upon docking the testing unit 405 to the doctor's workstation 410, the background and physiologic data may be automatically uploaded to the doctor's workstation 410. The application 1004 may then interrogate the doctor's workstation 405 after the clinician replies affirmatively to the application's prompt in step 1135. Of course the doctor's workstation 410 may be omitted and the testing unit 405 may interact directly with the application 1004.

After the background and physiologic data has been uploaded to the application 1004, the application may choose, in step 1140, one or more discriminant equations that are applicable to the transferred data. For example, the application 1004 may have previously derived two discriminatory equations from a population of data. One equation may identify a pattern that discriminates between a population of individuals with normal autonomic function and individuals with abnormal autonomic function. Another equation may discriminate between 30 year black men with hypertension and 30-year-old black men without hypertension. If the clinician sends data to the application 1004 concerning a 30-year-old black man, the application 1004 may choose both equations for application 1004 to the new patient data. If the clinician transmits data from a 50-year-old white woman, the application may only select the equation that discriminates broadly between individuals with normal autonomic function and those without normal autonomic function.

In step 1145, the application 1004 applies the new patient data to the selected equations and generates one or more ADRs or autonomic rankings. In step 1150, the application 1004 may incorporate the autonomic ranking into a report that may be saved on the server 1001, in step 1155, and/or be sent over the internet 1003 to the doctor's workstation 410 or testing unit 405 in step 1160. Then, considering the test is complete and a report has been sent to the clinician, in step 1165, the application 1004 may decrease the number of available credits for studies the clinician has purchased by one. The application may then prompt the clinician to order additional tests if less than a predetermined number of tests are then available to the clinician. The process may then end in step 1170.

The physiologic data that may be sent in step 1135 may be, for example, raw ECG data or processed ECG data. Thus, the ECG data from a patient's HRV study may be sent in the form it was collected as to the application 1004. The ECG data may be, however, sent to the application 1004 only after artifact and abnormal heartbeats have been removed using the processes described above. Yet again, the ECG data may be analyzed locally thus deriving values or HRV parameters such as SDNN or RMS-SD. These HRV parameters may be sent alone to the application 1004 or may be derived by the application 1004 from ECG data previously sent to the application 1004. In order to create more comprehensive and increasingly accurate normative databases, newly acquired raw ECG data and/or processed ECG data and/or physiologic parameters or values may all be sent to the server 1001 for further analysis at, for example, a later time.

The application 1004 is not limited to the HRV sector. For example, the application 1004 may be used with other medical testing, such as in general spirometry testing. A clinician may choose a test from the application 1004. Upon transferring physiological data to the application 1004, the application 1004 may analyze the data and return results to the clinician or provide other services that allow the clinician to analyze the data. Upon purchasing a test from the application 1004, the application 1004 may bill the clinician for a spirometric mouthtube if such a device is needed to perform the test. Various blood tests could be used with the model as well. Upon purchasing a test from the application 1004, the clinician could be billed for a testing kit that might include a syringe, blood tube, bandages and other related equipment.

In addition, ECG analysis services are within the scope of the invention. Rather than providing expensive ECG analysis technologies within a clinician's office, physiological data (eg., ECG data) could be transmitted to the application 1004 whereby the ECG data is analyzed and test results are returned to the clinician. The process could be repeated for that patient at later dates. Then, the application 1004 could display the various ECG tests to the clinician, using a browser 1002, to quickly illustrate differences in the patient's ECG recordings over time. This aspect of the invention would be of paramount importance by an emergency room clinician that must quickly access a patient's medical records without waiting for files to be forwarded to the emergency room. The clinician could use the internet to access ECG files located on the server 1001. Using a unique identifier associated with each ECG test, the application 1004 could bill the clinician for, as an example, ECG patches and the like.

While various examples have been described above for using the ASP model, one of ordinary skill in the art will realize that any number of medical services may be provided with the ASP model and that those services are encompassed within the scope of the present invention.

Figure 12:
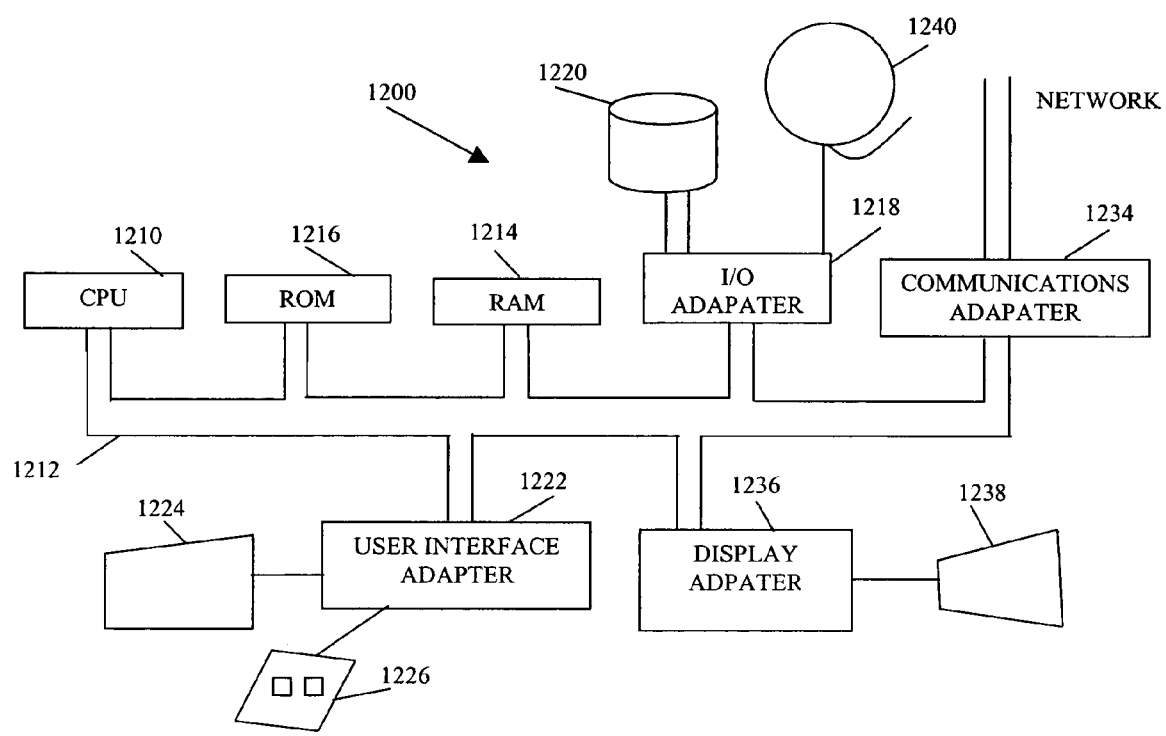
FIG. 12 is a data processing system that may be used for implementing various embodiments of the present invention.

Referring to FIG. 12, an example is shown of a data processing system 1200, which may be used for implementing any of the aforementioned embodiments of the invention, including one or more of the client machines 1002 and the web server 1001. The system has a central processing unit (CPU) 1210, which is coupled to various other components by system bus 1212. Read only memory ("ROM") 1216 is coupled to the system bus 1212 and includes a basic input/output system ("BIOS") that controls certain basic functions of the data processing system 1200. Random access memory ("RAM") 1214, I/O adapter 1218, and communications adapter 1234 are also coupled to the system bus 1212. I/O adapter 1218 may be a small computer system interface ("SCSI") adapter that communicates with a disk storage device 1220. Communications adapter 1234 interconnects bus 1212 with an outside network enabling the data processing system to communicate with other such systems. Input/Output devices are also connected to system bus 1212 via user interface adapter 1222 and display adapter 1236. Keyboard 1224 and mouse 1226 are interconnected to bus 1212 via user interface adapter 1222. Display adapter 1236 connects display monitor 1238 to system bus 1212. In this manner, a user is capable of inputting to the system throughout the keyboard 1224 or mouse 1226 and receiving output from the system via display 1238.

Embodiments of the invention may be implemented as a computer system programmed to execute the method or methods described herein, and as a computer program product. According to the computer system implementation, sets of instructions for executing the method or methods are resident in the random access memory 1214 of one or more computer systems configured generally as described above. Those of ordinary skill in the art will appreciate that the computer program product or software program instructions are capable of being distributed as one or more program products, in a variety of forms. Processor 1210, from either a client machine 1002 and/or server computer 1001, may execute one or more of the computer program products stored in memory 1214. Client computer 1002 and server computer 1001 may be individually programmed to collectively execute the process or processes of the invention described herein. Until required by the computer system, the set of instructions may be stored as a computer program product in another computer memory, for example, in disk drive 1220 (which may include a removable memory such as an optical disk or floppy disk for eventual use in the disk drive 1220). Further, the computer program product can also be stored at another computer and transmitted when desired to the user's workstation by a network or by an external network such as the Internet. One of ordinary skill in the art would appreciate that the physical storage of the sets of instructions physically changes the medium upon which it is stored so that the medium carries computer readable information. The change may be electrical, magnetic, chemical, biological, or some other physical change. While it is convenient to describe the invention in terms of instructions, symbols, characters, or the like, the reader should remember that all of these and similar terms should be associated with the appropriate physical elements.

As yet another embodiment of the invention, an embodiment of the invention entails a networked data processing environment. The data processing environment is an arrangement, as previously described, of one or more client computers 1002 and server computers 1001 (generally "hosts") connected to each other by a network 1003, for example, the Internet. Users access information and interface with network 1003 and server computer 1001 through a client computer 1002.

Note that the invention may describe terms such as comparing, validating, selecting, identifying, or other terms that could be associated with a human operator. However, for at least a number of the operations described herein, which form part of at least one of the embodiments, no action by a human operator is required. The operations described are, in large part, machine operations processing electrical signals to generate other electrical signals.

Additionally, the foregoing detailed description has set forth various embodiments of the present invention via the use of block diagrams, flowcharts, and/or examples. It will be understood by those of ordinary skill in the art that each block diagram component, flowchart step, and operations and/or components illustrated by the use of examples can be implemented, individually and/or collectively, by a wide range of hardware, software, firmware, or any combination thereof. The present invention may be implemented as those of ordinary skill in the art will recognize, in whole or in part, in standard Integrated Circuits, Application Specific Integrated Circuits (ASICs), as a computer program running on a general-purpose machine having appropriate hardware, such as one or more computers, as firmware, or as virtually any combination thereof and that designing the circuitry and/or writing the code for the software or firmware would be well within the skill of one of ordinary skill in the art, in view of this disclosure. It will also be understood that certain of the above-described structures, functions and operations of the above-described embodiments are not necessary to practice the present invention and are included in the description simply for completeness of an example embodiment or embodiments. In addition, it will be understood that specific structures, functions and operations set forth in the above-referenced patents and publications can be practiced in conjunction with the present invention, but they are not essential to its practice. It is therefore to be understood that within the scope of the claims, the invention may be practiced otherwise than as specifically described without actually departing from the spirit and scope of the present invention. Finally, all patents, publications and standards referenced herein are hereby incorporated by reference.

What is claimed is:

1. A method for analyzing a physiological signal comprising the steps of:
    obtaining a physiological signal that comprises a set of waveforms followed by an additional waveform; wherein the set of waveforms comprises:
    a first waveform;
    a last waveform; and
    one or more intermediate waveforms located between the first waveform and the last waveform;
    obtaining a maximum slope for the first waveform, the last waveform and the one or more intermediate waveforms;
    obtaining a maximum slope for the additional waveform by performing the steps of:
    confirming the maximum slope for the additional waveform is greater than a minimum threshold; and
    confirming the maximum slope for the additional waveform is less than a maximum threshold; wherein the minimum threshold and the maximum threshold are derived from the maximum slopes for the first waveform, the last waveform and the one or more intermediate waveforms.

2. The method of claim 1 comprising the additional step of obtaining a second set of waveforms that is located between the set of waveforms and the additional waveform; wherein the second set of waveforms comprises one or more waveforms.

3. The method of claim 1 wherein the one or more intermediate waveforms comprise a predetermined number of waveforms.

4. The method of claim 3 wherein the predetermined number of waveforms is determined pursuant to empirical observation.

5. The method of claim 1 further comprising the step of calculating a mean value of the maximum slopes for the first waveform, the last waveform and the one or more intermediate waveforms.

6. The method of claim 5 wherein the minimum threshold is derived by multiplying the mean value by a predetermined value.

7. The method of claim 6 wherein the predetermined value is about 0.06.

8. The method of claim 5 wherein the maximum threshold is derived by multiplying the mean value by a predetermined value.

9. The method of claim 8 wherein the predetermined value is about 1.6.

10. The method of claim 1 further comprising the step of calculating a median value of the maximum slopes for the first waveform, the last waveform and the one or more intermediate waveforms.

11. The method of claim 10 wherein the minimum threshold is derived by multiplying the median value by a predetermined value.

12. The method of claim 11 wherein the predetermined value is about 0.06.

13. The method of claim 10 wherein the maximum threshold is derived by multiplying the median value by a predetermined value.

14. The method of claim 13 wherein the predetermined value is about 1.6.

15. The method of claim 1 further comprising the step of obtaining a cycle length between the maximum slope for the last waveform and the maximum slope for the additional waveform.

16. The method of claim 15 further comprising the step of determining whether the cycle length is less than a maximum cycle length.

17. The method of claim 16 wherein the maximum cycle length is about 2000 ms.

18. The method of claim 16 further comprising the step of obtaining a longest cycle length within the set of waveforms; wherein the maximum cycle length is derived from the longest cycle length within the set of waveforms.

19. The method of claim 16 wherein the physiological signal is filtered with a moving average filter and a band pass filter before maximum slopes are obtained for the first waveform, the last waveform and the one or more intermediate waveforms.

20. The method of claim 15 further comprising the step of determining whether the cycle length is greater than a minimum cycle length.

21. The method of claim 20 wherein the minimum cycle length is about 330 ms.

22. The method of claim 20 further comprising the step of obtaining a shortest cycle length within the set of waveforms; wherein the minimum cycle length is derived from the shortest cycle length within the set of waveforms.

23. The method of claim 1 wherein the physiological signal is filtered with a moving average filter and a band pass filter before maximum slopes are obtained for the first waveform, the last waveform and the one or more intermediate waveforms.

24. The method of claim 1 wherein the physiological signal is comprised of data selected from the group consisting of: ECG data, EMG data and EEG data.

25. One or more program storage media readable by a machine and containing instructions for performing the method contained in claim 1.

26. A system for analyzing a physiologic signal comprising:
one or more memory units operable for storing one or more computer products for assessing autonomic performance; and
one or more processors coupled to the one or more memory units, wherein the one or more processors execute the one or more computer products for performing the steps of:
obtaining a physiological signal that comprises a set of waveforms followed by an additional waveform; wherein the set of waveforms comprises:
a first waveform;
a last waveform; and
one or more intermediate waveforms located between the first waveform and the last waveform;
obtaining a maximum slope for the first waveform, the last waveform and the one or more intermediate waveforms;
obtaining a maximum slope for the additional waveform by performing the steps of:
confirming the maximum slope for the additional waveform is greater than a minimum threshold; and
confirming the maximum slope for the additional waveform is less than a maximum threshold; wherein the minimum threshold and the maximum threshold are derived from the maximum slopes for the first waveform, the last waveform and the one or more intermediate waveforms.

27. The system of claim 26 wherein the one or more processors execute the one or more computer products for performing the additional step of obtaining a second set of waveforms that is located between the set of waveforms and the additional waveform; wherein the second set of waveforms comprises one or more waveforms.

28. The system of claim 26 wherein the one or more intermediate waveforms comprise a predetermined number of waveforms.

29. The system of claim 28 wherein the predetermined number of waveforms is determined pursuant to empirical observation.

30. The system of claim 29 wherein the one or more processors execute the one or more computer products for performing the additional step of calculating a mean value of the maximum slopes for the first waveform, the last waveform and the one or more intermediate waveforms.

31. The system of claim 30 wherein the minimum threshold is derived by multiplying the mean value by a predetermined value.

32. The system of claim 31 wherein the predetermined value is about 0.06.

33. The system of claim 30 wherein the maximum threshold is derived by multiplying the mean value by a predetermined value.

34. The system of claim 33 wherein the predetermined value is about 1.6.

35. The system of claim 26 wherein the one or more processors execute the one or more computer products for performing the additional step of calculating a median value of the maximum slopes for the first waveform, the last waveform and the one or more intermediate waveforms.

36. The system of claim 35 wherein the minimum threshold is derived by multiplying the median value by a predetermined value.

37. The system of claim 36 wherein the predetermined value is about 0.06.

38. The system of claim 35 wherein the maximum threshold is derived by multiplying the median value by a predetermined value.

39. The system of claim 38 wherein the predetermined value is about 1.6.

40. The system of claim 26 wherein the one or more processors execute the one or more computer products for performing the additional step of obtaining a cycle length between the maximum slope for the last waveform and the maximum slope for the additional waveform.

41. The system of claim 40 wherein the one or more processors execute the one or more computer products for performing the additional step of determining whether the cycle length is less than a maximum cycle length.

42. The system of claim 41 wherein the maximum cycle length is about 2000 ms.

43. The system of claim 41 wherein the one or more processors execute the one or more computer products for performing the additional step of obtaining a longest cycle length within the set of waveforms; wherein the maximum cycle length is derived from the longest cycle length within the set of waveforms.

44. The system of claim 41 further comprising a moving average filter and a band pass filter for filtering the physiological signal.

45. The system of claim 41 wherein the one or more processors execute the one or more computer products for performing the additional step of filtering the physiological signal with a moving average filter and a band pass filter before maximum slopes for the first waveform, the last waveform and the one or more intermediate waveforms are obtained.

46. The system of claim 40 wherein the one or more processors execute the one or more computer products for performing the additional step of determining whether the cycle length is greater than a minimum cycle length.

47. The system of claim 46 wherein the minimum cycle length is about 330 ms.

48. The system of claim 46 wherein the one or more processors execute the one or more computer products for performing the additional step of obtaining a shortest cycle length within the set of waveforms; wherein the minimum cycle length is derived from the shortest cycle length within the set of waveforms.

49. The system of claim 26 further comprising a moving average filter and a band pass filter for filtering the physiological signal.

50. The system of claim 26 wherein the physiological signal is comprised of data selected from the group consisting of: ECG data, EMG data and EEG data.

51. A method for analyzing a physiological signal comprising the steps of:
obtaining a physiological signal that comprises a set of waveforms followed by an additional waveform; wherein the set of waveforms comprises:
a first waveform;
a last waveform; and
one or more intermediate waveforms located between the first waveform and the last waveform;
obtaining a fiduciary point for the first waveform, the last waveform, the one or more intermediate waveforms and the additional waveform;
obtaining a cycle length between the fiduciary point for the last waveform and the fiduciary point for the additional waveform;

obtaining a longest cycle length within the set of waveforms;

obtaining a shortest cycle length within the set of waveforms;

obtaining a verified fiduciary point for the additional waveform by performing the steps of:

confirming the cycle length is less than a maximum cycle length; and confirming the cycle length is greater than a minimum cycle length; wherein the maximum cycle length is derived from the longest cycle length within the set of waveforms and the minimum cycle length is derived from the shortest cycle length within the set of waveforms.

52. The method of claim 51 comprising the additional step of obtaining a second set of waveforms that is located between the set of waveforms and the additional waveform; wherein the second set of waveforms comprises one or more waveforms.

53. The method of claim 51 wherein the one or more intermediate waveforms comprise a predetermined number of waveforms.

54. The method of claim 53 wherein the predetermined number of waveforms is determined pursuant to empirical observation.

55. The method of claim 51 wherein the fiduciary points for the first waveform, the last waveform, the one or more intermediate waveforms and the additional waveform are derived from a maximum slope for the first waveform, the last waveform, the one or more intermediate waveforms and the additional waveform.

56. The method of claim 51 wherein the fiduciary points for the first waveform, the last waveform, the one or more intermediate waveforms and the additional waveform are derived from a peak amplitude for the first waveform, the last waveform, the one or more intermediate waveforms and the additional waveform.

57. The method of claim 51 wherein the maximum cycle length is about 2000 ms.

58. The method of claim 51 wherein the minimum cycle length is about 330 ms.

59. The method of claim 51 wherein the physiological signal is filtered with a moving average filter and a band pass filter before fiduciary points are obtained for the first waveform, the last waveform and the one or more intermediate waveforms.

60. One or more program storage media readable by a machine and containing instructions for performing the method contained in claim 51.

* * * * *